(12) United States Patent
Baltimore et al.

(10) Patent No.: US 6,822,070 B2
(45) Date of Patent: Nov. 23, 2004

(54) TRUNCATED CRAF1 INHIBITS CD40 SIGNALING

(76) Inventors: David Baltimore, 508 Union Wharf, Boston, MA (US) 02109; Genhong Cheng, 827 Leverin Ave., Apt. 304, Los Angeles, CA (US) 90024; Zheng-Sheng Ye, 1233 York Ave., New York, NY (US) 10021; Seth Lederman, 533 W. 112th St., Apt. 8C, New York, NY (US) 10025; Aileen Cleary, 60 Haven Ave., New York, NY (US) 10032

( * ) Notice: Subject to any disclaimer, the term of this patent is extended or adjusted under 35 U.S.C. 154(b) by 31 days.

(21) Appl. No.: 08/813,323

(22) Filed: Mar. 10, 1997

(65) Prior Publication Data

US 2002/0031522 A1 Mar. 14, 2002

Related U.S. Application Data

(60) Provisional application No. 60/013,199, filed on Mar. 11, 1996.

(51) Int. Cl.[7] .................................................. C07K 5/00
(52) U.S. Cl. ...................... 530/300; 530/300; 435/7.1; 424/184.1; 424/185.1
(58) Field of Search ...................... 424/185.1; 435/4.23, 435/7.2; 436/63, 64; 530/324, 350, 358

(56) References Cited

FOREIGN PATENT DOCUMENTS

WO        WO9533051        12/1995

OTHER PUBLICATIONS

Burgess et al. Journal of Cell Biology, 1990, 11: 2129–2138.*

Straub, P. J. Biol. Chem. 268 (29): 21997–23003, 1993.*

Kouklis PD. J. Cell Science, 106(pt 3):919–28, 1993.*

Sato et al. "A novel member of the TRAF family of putative signal transducing proteins binds to the cytosolic domain of CD40" Febs Letters. vol. 358 pp. 113–118, Jan. 23, 1995.*

Cheng, Genhong et al. (1995) Involvement of CRAF1, A Relative of TRAF, in CD40 Signaling. *Science* 267:1494–1498.

Hu, Hong Ming et al. (1994) A Novel RING Finger Protein Interacts with the Cytoplasmic Somain of CD40. *J. Bio. Chem.* 269: 30069–30072.

Mosialos, George et al. (1995) The Epstein–Barr Virus Transforming Protein LMP1 Engages Signaling Proteins for the Tumor Necrosis Factor Receptor Family. *Cell* 80:389–399.

* cited by examiner

*Primary Examiner*—Susan Ungar
*Assistant Examiner*—Minh-Tam Davis
(74) *Attorney, Agent, or Firm*—John P. White; Cooper & Dunham LLP

(57) ABSTRACT

Overexpression of a CRAF1 (CD40 receptor-associated factor 1) gene truncated by 323 to about 414 amino acids at the amino inhibits CD40-mediated cell activation, and is used to treat conditions characterized by an unwanted level of CD40-mediated intracellular signaling.

2 Claims, 11 Drawing Sheets

```
M  MESSKKMDAAGTLQPNPPLKLQPDRGAG.SVLVPEQGGYKEKFVKTVEDK    49
H  --------SP-A--T------HT--S--TP-F------------------

M  YKCEKCRLVLCNPKQTECGHRFCESCMAALLSSSSPKCTACQESIIKDKV    99
H  ------H----S----------------------------------V----

M  FKDNCCKREILALQVYCRNEGRGCAEQLTLGHLLVHLKNECQFEELPCLR    149
H  ---------------I-----S-----------------D-H------V-

M  ADCKEKVLRKDLRDHVEKACKYREATCSHCKSQVPMIKLQKHEDTDCPCV    199
H  P----------------------------------------A---------

M  VVSCPHKCSVQTLLRSELSAHLSECVNAPSTCSFKRYGCVFQGTNQQIKA    249
H  --------------------------------------------------

M  HEASSAVQHVNLLKEWSNSLEKKVSLLQNESVEKNKSIQSLHNQICSFEI    299
H  --------------------------------------------------

M  EIERQKEMLRNNESKILHLQRVIDSQAEKLKELDKEIRPFRQNWEEADSM    349
H  --------------------------------------------------

M  KSSVESLQNRVTELESVDKSAGQAARNTGLLESQLSRHDQTLSVHDIRLA    399
H  ----------------------V------------------M--------

M  DMDLRFQVLETASYNGVLIWKIRDYKRRKQEAVMGKTLSLYSQPFYTGYF    449
H  --------------------------------------------------

M  GYKMCARVYLNGDGMGKGTHLSLFFVIMRGEYDALLPWPFKQKVTLMLMD    499
H  --------------------------------------------------

M  QGSSRRHLGDAFKPDPNSSSFKKPTGEMNIASGCPVFVAQTVLENGTYIK    549
H  --------------------------------------------------

M  DDTIFIKVIVDTSDLPDP                                    567
H  ------------------
```

*FIGURE 1*

```
M  MESSKKMDAAGTLQPNPPLKLQPDRGAG.SVLVPEQGGYKEKFVKTVEDK        49
H  --------SP-A--T------HT--S--TP-F-----------------

M  YKCEKCRLVLCNPKQTECGHRFCESCMAALLSSSSPKCTACQESIIKDKV        99
H  ------H----S-------------------------------V----

M  FKDNCCKREILALQVYCRNEGRGCAEQLTLGHLLVHLKNECQFEELPCLR        149
H  --------------I-----S-----------------D-H------V-

M  ADCKEKVLRKDLRDHVEKACKYREATCSHCKSQVPMIKLQKHEDTDCPCV        199
H  P------------------------------A-----------------

M  VVSCPHKCSVQTLLRSELSAHLSECVNAPSTCSFKRYGCVFQGTNQQIKA        249
H  -------------------------------------------------

M  HEASSAVQHVNLLKEWSNSLEKKVSLLQNESVEKNKSIQSLHNQICSFEI        299
H  -------------------------------------------------

M  EIERQKEMLRNNESKILHLQRVIDSQAEKLKELDKEIRPFRQNWEEADSM        349
H  -------------------------------------------------

M  KSSVESLQNRVTELESVDKSAGQAARNTGLLESQLSRHDQTLSVHDIRLA        399
H  ---------------------V----------------M----------

M  DMDLRFQVLETASYNGVLIWKIRDYKRRKQEAVMGKTLSLYSQPFYTGYF        449
H  -------------------------------------------------

M  GYKMCARVYLNGDGMGKGTHLSLFFVIMRGEYDALLPWPFKQKVTLMLMD        499
H  -------------------------------------------------

M  QGSSRRHLGDAFKPDPNSSSFKKPTGEMNIASGCPVFVAQTVLENGTYIK        549
H  -------------------------------------------------

M  DDTIFIKVIVDTSDLPDP                                        567
H  ------------------
```

FIGURE 3

| | CD40 binding | Fas binding | TNFαRII binding | Homo-dimerization |
|---|---|---|---|---|
| C26 (324–567) | + | - | - | + |
| C26NX (324–410) | - | ND | ND | - |
| C26ΔNB (324–487) | - | ND | ND | - |
| TRAF domain (356–567) | + | ND | ND | + |
| C26XC (415–567) | + | ND | ND | + |

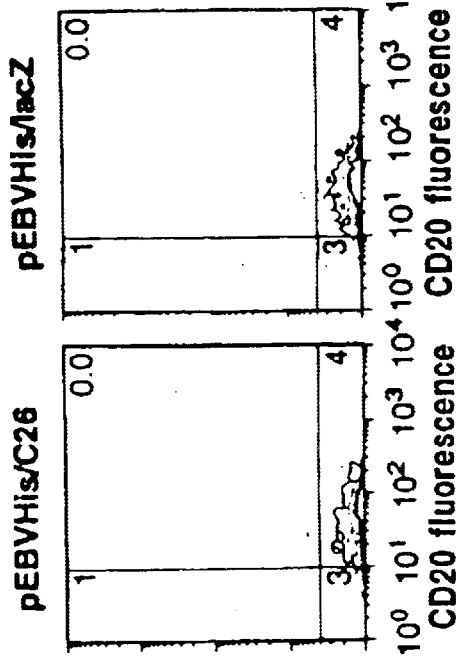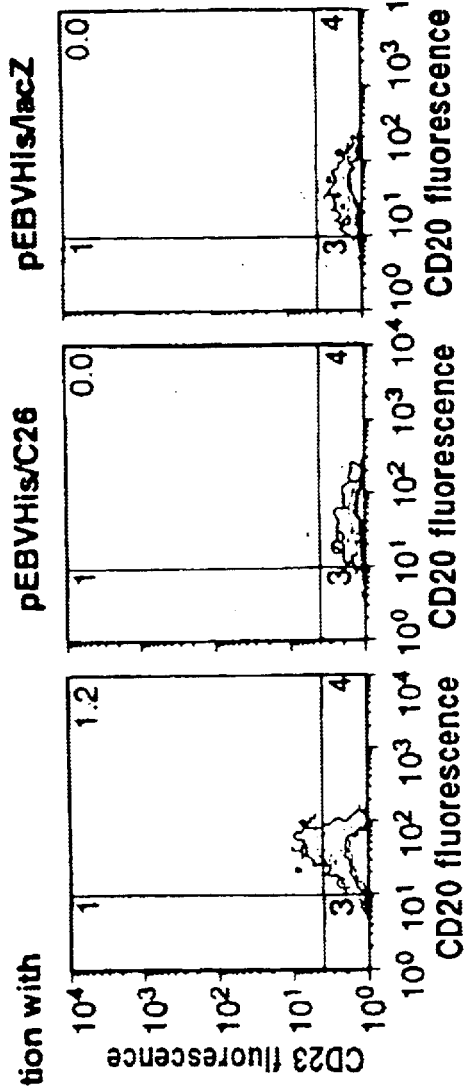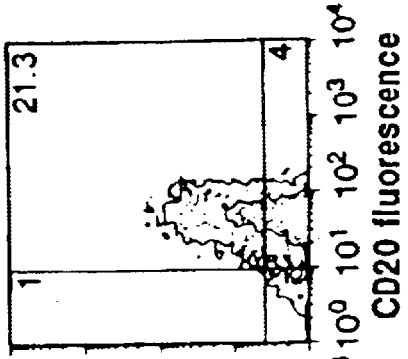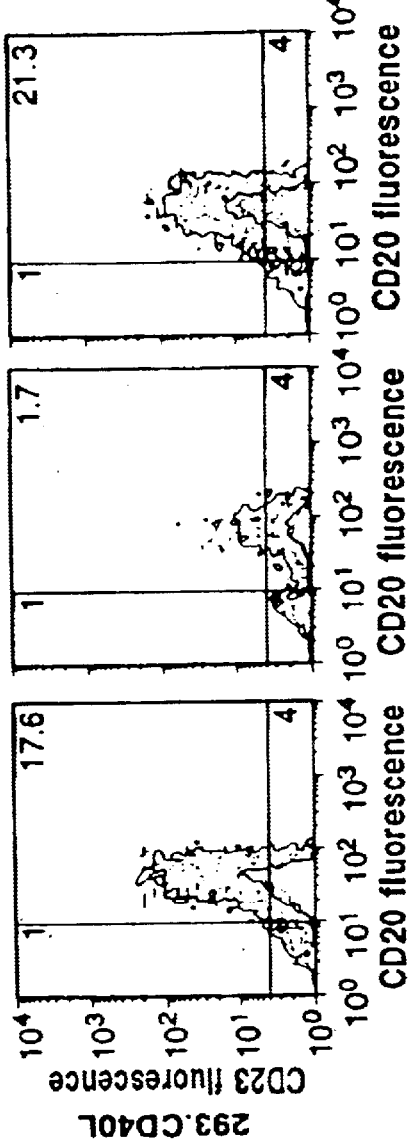

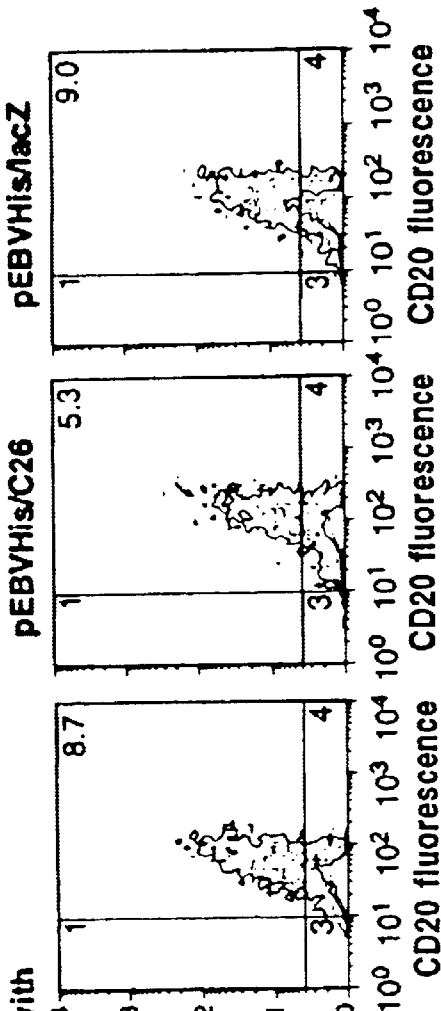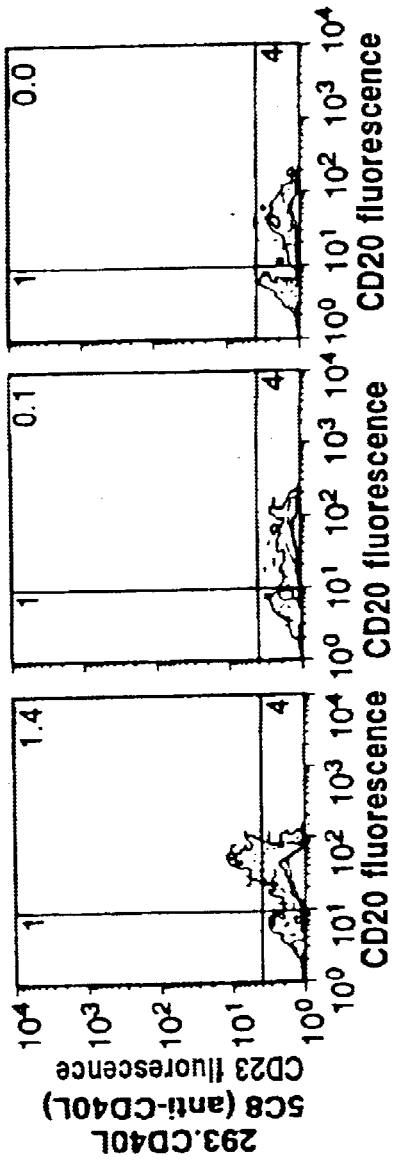

FIGURE 5A

```
   1 GGCGGCGGAG GATGCGGCGG GCGCCTGAGC CGGCCGAACG GGCGGCCTCG GGGTACAGGG
  61 TCCCCATTAC TTGAAGGATA AGGCTGGCAC GGCTCCGACG TCTGTGTGGA AGCTTCTCCC
 121 TCCCTTCTGA GCTTCTCTAG ACTCCTTACA GCGCACGGCA CAGAATTTCA GTTTCCTAAG
 181 ATGGAGTCAA GCAAAAAGAT GGATGCTGCT GGCACACTGC AGCCTAACCC ACCCCTAAAG
 241 CTGCAGCCTG ATCGCGGCGC AGGGTCCGTG CTCGTGCCGG AGCAAGGAGG CTACAAGGAG
 301 AAGTTTGTGA AGACAAGTAC AGACAAGTGA AAGTGCGAGA AGTGCCGCCT GGTGCTGTGC
 361 AACCCGAAGC AGACGGAGTG TGGCCACCGG TTCTGCGAGA GCTGCATGGC CGCCCTGCTG
 421 AGCTCCTCCA GTCCAAAATG CACAGCGTGC TCATCAAAGA CAAGGTGTTT
 481 AAGGATAATT GCTGCAAGAG AGAGATTCTG GCCCTTCAGG TCTACTGTCG GAATGAAGGC
 541 AGAGGTTGTG CGGAGCAGCT GACTCTGGGA CATCTGCTGG TGCACCTAAA AAATGAATGT
 601 CAGTTTGAGG AACTTCCCTG TCTGCGTGCC GACTGCAAAG AAAAAGTACT GAGAAAAGAC
 661 TTGCGGGATC ACGTGGAAAA GGCCTGTAAA TACCGCGAGG CCACGTGCAG TCACTGCAAG
 721 AGCCAAGTGC CCATGATCAA ACTGCAGAGA CATGAAGACA CAGATTGTCC CTGTGTGGTG
 781 GTATCCTGCC CTCACAAGTG CAGCGTTCAG ACTCTTCTAA GGAGTGAGTT GAGTGCACAC
 841 TTGTCCGAGT GTGTCAATGC CCCCAGCACC TGTAGTTTTA AGCGCTATGG CTGCGTTTTT
 901 CAGGGTACAA ACCAGCAGAT CAAGGCCCAT GAGGCCAGCT CCGGGTACA GCACGTGAAC
 961 CTGCTGAAGG AGTGGAGCAA CTCCCTGGAG AAGAAGGTTT CCCTGCTGCA GAATGAAAGT
1021 GTTGAGAAAA ACAAGAGCAT CCAAAGCCTG CACAACCAGA TCTGCAGCTT TGAGATCGAG
1081 ATTGAGAGGC AGAAGGAGAT GCTCCGAAAC AACGAGTCCA AGATCCTTCA CCTGCAGCGG
1141 GTAATCGACA GCCAAGCAGA GAAACTGAAA GAACTGGACA AGGAGATCCG TCCCTTCCGG
1201 CAGAACTGGG AGGAAGCGGA CAGCATGAAG AGCAGTGTGG AGTCCCTCCA GAACCGAGTG
1261 ACTGAGCTGG AGAGCGTAGA CAAAAGTGCG GGGCAGGCGG CTCCAACAC AGGCTTGCTG
1321 GAGTCCCAGC TGAGCCGGCA TGACCAGACG TTGAGTGTTC ATGACATCCG CTTGGCCGAC
1381 ATGGACCTGC GGTTCCAGGT CCTCGAGACC GCCAGTGCT ACGGGGTGCT GATCTGGAAG
1441 ATCCGTGACT ACAAGCGCCG GAAGCAGGAG GCCGTCATGG GGAAGACCCT GTCTCTCTAC
```

FIGURE 5B

```
1501 AGCCAGCCTT TCTACACAGG TTATTTTGGC TATAAGATGT GTGCCAGGGT CTACCTGAAT
1561 GGGGACGGAA TGGGAAAAGG GACACACTTG TCGCTGTTTT TTGTCATTAT GCGTGGAGAA
1621 TATGATGCTC TGTTGCCATG GCCGTTCAAG CAGAAAGTGA CACTTATGCT GATGGATCAG
1681 GGGTCCCTCT GCCGTCATCT GGGAGATGCG TTCAAGCCTG ACCCCAACAG CAGCAGCTTC
1741 AAGAAACCCA CCGGAGAGAT GAATATCGCC TCTGGCTGCC CAGTCTTTGT CGCCCAAACT
1801 GTTCTAGAGA ACGGGACGTA TATTAAAGAT GATACAATCT TTATTAAGGT CATAGTGGAT
1861 ACCTCGGATC TGCCTGACCC CTGACAAGAA AGCAGGGCGG TGGATTCAGC AGAAGGTAAAC
1921 TCCTCTGGGG GGGTGAGCTA GTGTCTTCAC GCCCTCAGAA AGGACCTTGT
1981 GGCGCAGAGG AAGCAGCCGG AGGAGGAGAA GGAGGTCGAG TGGCTGGCAG GAGAGCCACA
2041 TGTGAAAACA GACCCCAACG GATTTTCTAA TAAACTAGCC ACACCCACTC TGAAGGATTA
2101 TTTATCCATC AACAAGATAA ATACTGCTGT CAGAGAAGGT TTTCATTTTC ATTTTAAAAG
2161 ATCTAGTATT AAGGTGGGAA CATATATGCT AAAAAGAAAC ATGATTTTTC TTCCTTAACT
2221 TAAACACCAA AAAGAGAACA CATGTGGGGG TAGCTGGAGT GTGTACAGTA CCTCGAGGGC
2281 TTAAAATCAT AAACAATCAC ATACTCATCC TAAAATTCAG GGTGCAACTC CGTTTCAAAT
2341 ATTGTATATT GTCTATTTA
```

FIGURE 6A

```
   1 CGGGGAGCG CGGCGCGGCC GCCCCGTGCG CGAGCCGGGG TTGCAGCCCA GCCGGGACTT
  61 TCCAGCCGGC GGCAGCCGCG GCGGTCGTCG GCTCTTCCCC GCCCCCCGTC ATGGGGCAGC
 121 CCGGGAGCA GAACGCTGCG GACCGCGGCG GAGGACGCGC CCGGCGCGCC TGAGCCGGCC
 181 GAGCGGCGAC GGACCGCGAG AACTCCTCTT TCCTAAAAATG GAGTCGAGTA AAAAGATGGA
 241 CTCTCCTGGC GCCCTGCAGA CTAACCCGCC GCTAAAGCTG CACACTGACC GTAGTGCTGG
 301 GACGCCAGTT TTTGTCCCTG AACAAGGAGG TTACAAGGAA AAGTTTGTGA AGACCGTGGA
 361 GGACAAGTAC AAGTGTGAGA AGTGCCACCT GGTGCTGTGC AGCCCGAAGC AGACCGAGTG
 421 TGGGCACCGC TTCTGCGAGA GCTGCATGGC GGCCCTGCTG AGCTCTTCAA GTCCAAAATG
 481 TACAGCGTGT CAAGAGAGCA TCGTTAAAGA TAAGGTGTTT AAGGATAATT GCTGCAAGAG
 541 AGAAATTCTG GCTCTTCAGA TCTATTGTCG GAATGAAAGC AGAGGTTGTG CAGAGCAGTT
 601 AACGCTGGGA CATCTGCTGG TGCATTTAAA AAATGATTGC CATTTTGAAG AACTTCCATG
 661 TGTGCGTCCT GACTGCAAAG AAAAGGTCTT GAGGAAAGAC CTGCGAGACC ACGTGGAGAA
 721 GGCGTGTAAA TACCGGGAAG CCACATGCAG CCACTGCAAG AGTCAGGTTC CGATGATCGC
 781 GCTGCAGAAA CACGAAGACA CCGACTGTCC CTGCGTGGTG GTGTCCTGCC CTCACAAGTG
 841 CAGCGTCCAG ACTCTCCTGA GGAGCGAGTT GAGTGCACAC TTGTCAGAGT GTGTCAATGC
 901 CCCCAGCACC TGTAGTTTTA AGCGCTATGG CTGCGTTTTT CAGGGACAA ACCAGCAGAT
 961 CAAGCCCAC GAGGCCAGCT CCGCCGTGCA GCACGTCAAC CTGCTGAAGG AGTGGAGCAA
1021 CTCGCTCGAA AAGAAGGTTT CCTTGTTGCA GAATGAAAGT GTAGAAAAAA ACAAGAGCAT
1081 ACAAAGTTTG CACAATCAGA TATGTAGCTT GAAAATTGAA ATTGAGAGAC AAAAGGAAAT
1141 GCTTCGAAAT AATGAATCCA AAATCCTTCA TTTACAGCGA GTGATCGACA GCCAAGCAGA
1201 GAAACTGAAG GAGCTTGACA AGGAGATCCG GCCCTTCCGG CAGAACTGGG AGGAAGCAGA
1261 CAGCATGAAG AGCAGCGTGG AGTCCCTCCA GAACCGCGTG ACCGAGCTGG AGAGCGTGGA
1321 CAAGAGTGCG GGGCAAGTGG CTCGGAACAC AGGCCTGCTG GAGTCCCAGC TGAGCCGGCA
1381 TGACCAGATG CTGAGTGTGC ACGACATCCG CCTAGCCTGC ATGGACCTGC GCTTCCAGGT
1441 CCTGGAGACC GCCAGCTACA ATGGAGTGCT CATCTGGAAG ATTCGCGACT ACAAGCGGCG
```

FIGURE 6B

```
1501 GAAGCAGGAG GCCGTCATGG GGAAGACCCT GTCCCTTTAC AGCCAGCCTT TCTACACTGG
1561 TTACTTTGGT TATAAGATGT GTGCCAGGGT CTACCTGAAC GGGGACGGGA TGGGGAAGGG
1621 GACGCACTTG TCGCTGTTTT TTGTCATCAT GCGTGGAGAA TATGATGCCC TGCTTCCTTG
1681 GCCGTTTAAG CAGAAAGTGA CACTCATGCT GATGGATCAG GGGTCCTCTC GACGTCATTT
1741 GGGAGATGCA TTCAAGCCCG ACCCCAACAG CAGCAGCTTC AAGAAGCCCA CTGGAGAGAT
1801 GAATATCGCC TCTGGCTGCC CAGTCTTTGT GCCCCAAACT GTTCTAGAAA ATGGGACATA
1861 TATTAAAGAT GATACAATTT TTATTAAAGT CATAGTGGAT ACTTCGGATC TGCCCGATCC
1921 CTGATAAGTA GCTGGGGAGG TGGATTTAGC AGAAGGCAAC TCCTCTGGGG GATTTGAACC
1981 GGTCTGTCTT CACTGAGGTC CTCGCGCTCA GAAAAGACC TTGTGAGACG GAGGAAGCGG
2041 CAGAAGGCGG ACGCGTGCCG GCGGGAGGAG CCACGCGTGA GCACACCTGA CACGTTTTAT
2101 AATAGACTAG CCACACTTCA CTCTGAAGAA TTATTTATCC TTCAACAAGA TAAATATTGC
2161 TGTCAGAGAA GGTTTTCATT TTCATTTTTA AAGATCTAGT TAATTAAGGT GGAAAACATA
2221 TATGCTAAAC AAAAGAAACA TGATTTTTCT TCCTTAAACT TGAACACCAA AAAAACACAC
2281 ACACACACAC ACGTGGGGAT AGCTGGACAT GTCAGCATGT TAAGTAAAAG GAGAATTTAT
2341 GAAATAGTAA TGCAATTCTG ATATCTTCTT TCTAAAATTC AAGAGTGCAA TTTTGTTTCA
2401 AATACAGTAT ATTGTCTATT TTTAAGGCCT CCAAAAAAAA AAAAAATTCC GGCCG
```

US 6,822,070 B2

TRUNCATED CRAF1 INHIBITS CD40 SIGNALING

This application claims the benefit of U.S. Provisional No. 60/013,199, filed Mar. 11, 1996, the contents of which are hereby incorporated by reference into the present application.

The invention disclosed herein was made with Government support under NIH Grant Nos. RO1-CA55713 and A122346 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found in the text and at the end of this application, preceding the sequence listing and the claims.

The following standard abbreviations are used throughout to refer to amino acids:

| A | Ala | Alanine | M | Met | Methionine |
|---|-----|---------|---|-----|------------|
| C | Cys | Cysteine | N | Asn | Asparagine |
| D | Asp | Aspartic acid | P | Pro | Proline |
| E | Glu | Glutamic acid | Q | Gln | Glutamine |
| F | Phe | Phenylalanine | R | Arg | Arginine |
| G | Gly | Glycine | S | Ser | Serine |
| H | His | Histidine | T | Thr | Threonine |
| I | Ile | Isoleucine | V | Val | Valine |
| K | Lys | Lysine | W | Trp | Tryptophan |
| L | Leu | Leucine | Y | Tyr | Tyrosine |

BACKGROUND OF THE INVENTION

CD40 (1) is a receptor on B cells that interacts with the helper T cell surface protein CD40L (CD40 ligand, also known as T-BAM, gp39, or TRAP) (2–4). CD40L is found particularly on lymphoid follicle CD4$^+$ T lymphocytes, where it delivers a contact-dependent signal that stimulates B cell survival, growth, and differentiation (2–4). Signaling through CD40 rescues B cells from apoptosis induced by Fas (CD95) or by cross-linking of the immunoglobulin M (IgM) complex (5); it also induces B cells to differentiate and to undergo Ig isotype switching (3) and to express CD80 (B7 or BB-1) (6). The crucial role of CD40L-CD40 interaction is illustrated by humans with defects in CD40L, who manifest a serious immune deficiency syndrome, the X-linked hyper-IgM syndrome (HIGMX-1) characterized by an absence of IgG, IgA, and IgE, elevated IgM, and no lymphoid follicles (7). The essential roles of CD40L and CD40 in the phenotype of HIGMX-1 syndrome has been confirmed by targeted disruption of either CD40L (8) or CD40 (9) in mice. In addition to B cells, CD40 is also expressed by follicular dendritic cells (10), dendritic cells (11), activated macrophages (12), epithelial cells (including thymic epithelium) (13), and a variety of tumor cells.

Stimulation of CD40 causes the tyrosine phosphorylation of multiple substrates including Src family kinases such as p53–p56$^{lyn}$, activates multiple serine-threonine-specific protein kinases, and induces the phosphorylation of phospholipase C-γ2 and of phosphoinositide-3' kinase (14).

In mice the CD40 cytoplasmic tail is necessary for signaling (15). Proteins which interact with the cytoplasmic tail of CD40 have been described (H. M. Hu, et al., *J. Biol. Chem.* 269: 30069 (1994); and G. Mosialos, et al., *Cell* 80:389 (1995)). These proteins are the same as CRAF1.

SUMMARY OF THE INVENTION

This invention provides a protein comprising CRAF1 truncated by from about 323 to about 414 amino acid residues at the amino terminus, or a variant thereof capable of inhibiting CD40-mediated cell activation.

This invention provides a method of inhibiting activation by CD40 ligand of cells bearing CD40 on the cell surface, comprising providing the cells with an agent capable of inhibiting CD40-mediated intracellular signaling, the agent being present in an amount effective to inhibit activation of the cells.

This invention provides a method of providing a subject with an amount of a protein comprising CRAF1 truncated by from about 323 to about 414 amino acid residues at the amino terminus, or a variant thereof effective to inhibit activation by CD40 ligand of cells bearing CD40 on the cell surface in the subject, comprising: introducing into CD40-bearing cells of the subject, a nucleic acid sequence encoding the protein under conditions such that the cells express in the subject an activation inhibiting effective amount of the protein.

This invention provides a method of treating a condition characterized by an aberrant or unwanted level of CD40-mediated intracellular signaling, in a subject, comprising providing the subject with a therapeutically effective amount of an agent capable of inhibiting CD40-mediated intracellular signaling in cells bearing CD40 on the cell surface.

This invention provides a nucleic acid molecule encoding a protein comprising CRAF1 truncated by from about 323 to about 414 amino acid residues at the amino terminus, or a variant thereof capable of inhibiting CD40-mediated cell activation.

This invention provides a method of identifying an agent capable of inhibiting CD40-mediated intracellular signaling in a cell expressing CD40 on the cell surface, comprising providing the cell with the agent under conditions permitting activation of the cell in the absence of the agent, and determining decreased or absent activation, thereby identifying an agent capable of inhibiting CD40-mediated intracellular signaling in a cell expressing CD40 on the cell surface.

DESCRIPTION OF THE FIGURES

FIG. 1. Predicted amino acid sequences of mouse (M) (SEQ ID NO:1) and human (H) (SEQ ID NO:2) CRAF1. The full-length mouse sequence is shown and numbered. The human sequence has one more amino acid than that of the mouse (indicated with a dot), but all numbers here refer to the mouse sequence. Dashes indicate positions in the human sequence that are identical to those in the mouse. The C26 clone obtained from the yeast two-hybrid screen contained the COOH-terminal region of CRAF1 starting from the position marked with an arrow.

FIG. 3. Mapping the CD40 binding and homodimerization domain of CRAF1. C26NX and C26XC represent fragments from the NH$_2$-terminus of C26 to the internal XhoI site and from the XhoI site to the COOH-terminus of CRAF1, respectively. C26ΔNB was made by the deletion of the NcoI-Bgl II fragment in the 3' untranslated region of the C26 cDNA clone. The full TRAF domain of CRAF1 was synthesized by the polymerase chain reaction with the use of plaque-forming units of DNA polymerase. Various DNA fragments were ligated in-frame into yeast expression vectors encoding either the LexA DNA-binding domain (LexA) or the transcriptional activation domain (TAD). For CD40 binding assays, the LexA construct containing the CD40 cytoplasmic tail and various TAD fusion constructs were cotransfected into yeast strain EGY48 along with the lacZ-containing reporter vector (pSH18-34). Colonies that grew up on synthetic dextrose plates without tryptophan, uracil, and histidine were replica-plated to plates with or without leucine and tested for galactose-inducible blue color in the presence of x-gal. LexA constructs containing the cytoplasmic tails of Fas and TNFαRII were also included in the same experiments to test their interaction with the C26 clone. For dimerization assays, various LexA fusion constructs containing different fragments of C26 were used in every combination with various TAD fusion constructs. Transformants that grew on plates lacking leucine and that showed galactose-inducible blue are marked "+"; this was further confirmed by β-galactosidase assays with the use of yeast grown in liquid cultures (34). Transformants that grew only on plates containing leucine but that did not show blue on x-gal plates are marked "−"; ND, experiments not done.

FIGS. 4A–M. Effect of C26 fusion proteins on CD40L; CD40-induced CD23 up-regulation. (A) Northern blot analysis of Ramos 2G6 transfectants. Total RNA (2 μg) from the Jurkat T cell line (B2.7) was used for markers. In other lanes, polyadenylate-containing RNA (0.75 μg per lane) was obtained from the untransfected Ramos 2G6 clone (Ramos) or pEBVHis/C26 Ramos transfectants (B6, C5, or D10). RNA blots of control and transfected cell lines were probed with C26 cDNA or an actin probe. (B-M) Two-color fluorescence-activated cell sorting analysis of Ramos 2G6 and Ramos 2G6 transfectants (pEBVHis/C26 or pEBVHis/lacZ) after 18 to 24 hours of culture with medium (-), 293.CD40L cells, rIL-4, or 293.CD40 cells plus anti-CD40L mAB 5C8 (as indicated). The x and y axes represent CD20 and CD23 fluorescence, respectively. The percentage of CD20$^+$ cells that express CD23 is indicated in the upper right-hand corner of each contour map. The D10 clone of pEBVHis/C26 is shown.

FIGS. 5A–B. cDNA nucleotide sequence and predicted amino acid sequences of mouse CRAF1 (SEQ ID NO:4). The cDNA nucleotide sequence is also deposited in GenBank with accession number U21050.

FIGS. 6A–B. cDNA nucleotide sequence and predicted amino acid sequences of human CRAF1 (SEQ ID NO:5). The cDNA nucleotide sequence is also deposited in GenBank with accession number U21092.

DETAILED DESCRIPTION

Figure 2A:
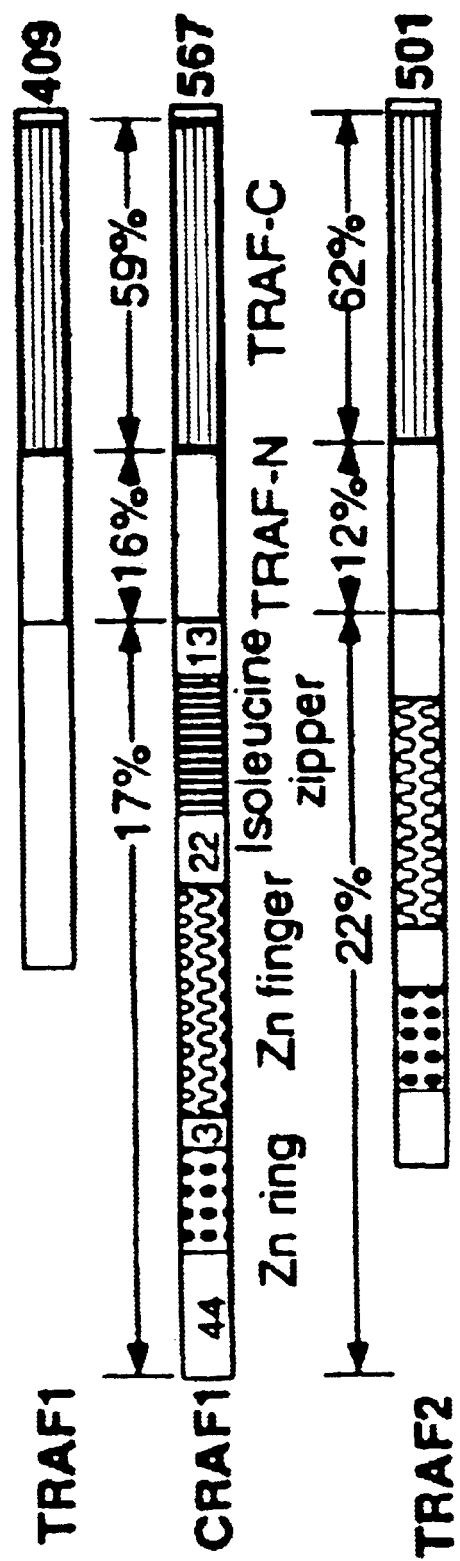
FIGS. 2A–D. Potential structural domains of CRAF1. (A) Diagrams of three TRAF family members. Percentages of amino acid identity between CRAF1 and either TRAF1 or TRAF2 are shown. The TRAF domain was defined in the COOH-terminal region of TRAF1 and TRAF2(19) (residues 356 to 562 for CRAF1 (SEQ ID NO:6)) but can be subdivided into TRAF-N and TRAF-C subregions according to sequence homology with CRAF1 as will as by the mapping assaying shown in FIG. 3. For CRAF1 (SEQ ID NO:1), the number of amino acids between homologous regions is indicated. (B) Helical wheel representation of residues 287 to 342 of CRAF1 (SEQ ID NO:7). The wheel starts with the inner residue Ile$^{287}$ at position a and diminishes with the outer residue Asn$^{342}$ at position g; "+" and "−" denote change of amino acid residues. (C) Predicted Zn fingers corresponding to residues 110 to 264 of CRAF1 (SEQ ID NO:8). (D) Zn finger from residues 45 to 106 of CRAF1 (SEQ ID NO:9). n, NH$_2$-terminus; c, COOH-terminus.
Figure 2B:
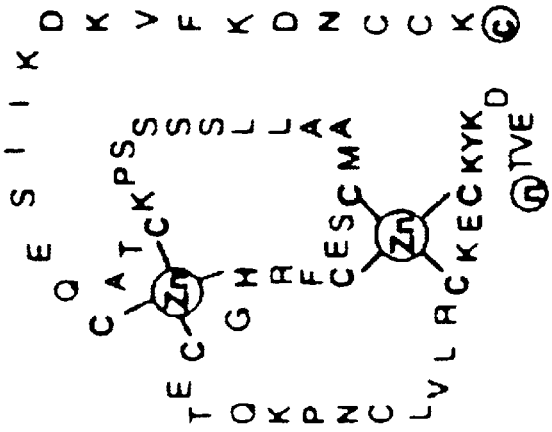
Figure 2D:
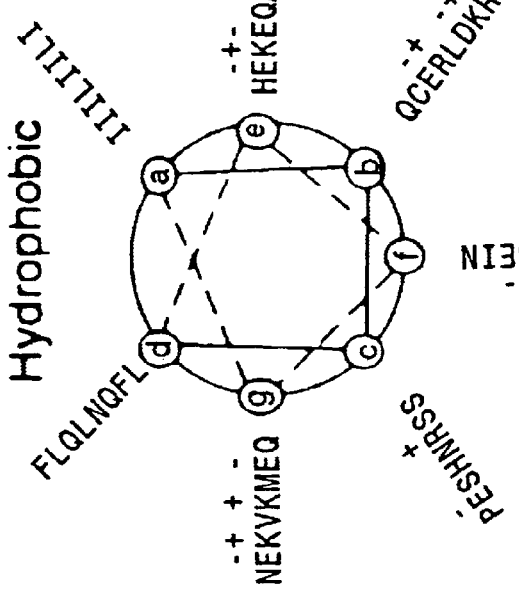

This invention provides a protein comprising CRAF1 truncated by from about 323 to about 414 amino acid residues at the amino terminus, or a variant thereof capable of inhibiting CD40-mediated cell activation. In an embodiment the variant comprises a conservative amino acid substitution.

Variants can differ from naturally occurring CD40 or CD40 ligand in amino acid sequence or in ways that do not involve sequence, or both. Variants in amino acid sequence are produced when one or more amino acids in naturally occurring CD40 or CD40 ligand is substituted with a different natural amino acid, an amino acid derivative or non-native amino acid. When a nucleic acid molecule encoding the protein is expressed in a cell, one naturally occurring amino acid will generally be substituted for another. Conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from Table 1, and yet others are described by Dayhoff in the Atlas of Protein Sequence and Structure (1988).

TABLE 1

Conservative Amino Acid Replacements

| For Amino Acid | Code | Replace with any of |
|---|---|---|
| Alanine | A | D-Ala, Gly, beta-ALa, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3,4 or 5-phenylproline, cis 3,4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met(O) D-Met(O), Val, D-Val |

TABLE 1-continued

Conservative Amino Acid Replacements

| For Amino Acid | Code | Replace with any of |
|---|---|---|
| Tyrosine | Y | D-Tyr,Phe, D-Phe, L-Dopa, His,D-His |
| Valine | V | D-Val, Leu,D-Leu,Ile,D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D- instead of L-amino acids into the polypeptide may increase its resistance to proteases. See, e.g., U.S. Pat. No. 5,219,990.

The protein of this invention may also be modified by various changes such as insertions, deletions and substitutions, either conservative or non-conservative where such changes might provide for certain advantages in their use.

In other embodiments, variants with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Variants within the scope of the invention include proteins and peptides with amino acid sequences having at least eighty percent homology with the COOH-terminal domain of CRAF1 (corresponding roughly to residues 415–567 (SEQ ID NO:12)) or with C26 (residues 324–567 of CRAF1 (SEQ ID NO:11)). More preferably the sequence homology is at least ninety percent, or at least ninety-five percent.

Just as it is possible to replace substituents of the scaffold, it is also possible to substitute functional groups which decorate the scaffold with groups characterized by similar features. These substitutions will initially be conservative, i.e., the replacement group will have approximately the same size, shape, hydrophobicity and charge as the original group. Non-sequence modifications may include, for example, in vivo or in vitro chemical derivatization of portions of the protein of this invention, as well as changes in acetylation, methylation, phosphorylation, carboxylation or glycosylation.

In a further embodiment the protein is modified by chemical modifications in which activity is preserved. For example, the proteins may be amidated, sulfated, singly or multiply halogenated, alkylated, carboxylated, or phosphorylated. The protein may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of the protein, for example the methionine sulfone and methionine sulfoxide analogs. The invention also includes salts of the proteins, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

In specific embodiments the CRAF1 is mouse or human CRAF1.

This invention provides a method of inhibiting activation by CD40 ligand of cells bearing CD40 on the cell surface, comprising providing the cells with an agent capable of inhibiting CD40-mediated intracellular signaling, the agent being present in an amount effective to inhibit activation of the cells. In an embodiment the agent is a protein comprising CRAF1 truncated by from about 323 to about 414 amino acid residues at the amino terminus, or a variant thereof.

In an embodiment of the method of inhibiting activation by CD40 ligand of cells bearing CD40 on the cell surface, the cells are provided with the protein of this invention by introducing into the cells a nucleic acid sequence encoding the protein under conditions such that the cells express an amount of the protein effective to inhibit activation of the cells. The nucleic acid may be DNA (including cDNA) or RNA. It may be single or double stranded, linear or circular. It may be in the form of a vector such as a plasmid or a viral vector. Preferably the nucleic acid sequence is operably linked to a transcriptional control sequence recognized by the host cell.

In another embodiment the agent is a small molecule. As used herein a small molecule is a compound capable of entering the cell. Preferably it has a molecular weight between 20 Da and $1 \times 10^6$ Da, preferably from 50 Da to 2 kDa.

In an embodiment the agent is modified from a lead inhibitory agent. In an embodiment the agent specifically binds to CD40 intracellular domain.

In embodiments of the methods described herein, the CD40-bearing cells are selected from the group consisting of B cells, fibroblasts, endothelial cells, epithelial cells, T cells, basophils, macrophages, Reed-Steinberg cells, dendritic cells, renal cells, and smooth muscle cells.

In a more specific embodiment the B cells are resting B cells, primed B cells, myeloma cells, lymphocytic leukemia B cells, or B lymphoma cells. In another specific embodiment the epithelial cells are keratinocytes. In another embodiment the fibroblasts are synovial membrane fibroblasts, dermal fibroblasts, pulmonary fibroblasts, or liver fibroblasts. In another specific embodiment the renal cells are selected from the group consisting of glomerular endothelial cells, mesangial cells, distal tubule cells, proximal tubule cells, parietal epithelial cells (e.g., crescent parietal epithelial cells), visceral epithelial cells, cells of a Henle limb, and interstitial inflammatory cells. In another embodiment the smooth muscle cells are smooth muscle cells of the bladder, vascular smooth muscle cells, aortic smooth muscle cells, coronary smooth muscle cells, pulmonary smooth muscle cells, or gastrointestinal smooth muscle cells. In a more specific embodiment the gastrointestinal smooth muscle cells are esophageal smooth muscle cells, stomachic smooth muscle cells, smooth muscle cells of the small intestine, or smooth muscle cells of the large intestine.

This invention provides a method of providing a subject with an amount of the protein of this invention effective to inhibit activation by CD40 ligand of cells bearing CD40 on the cell surface in the subject, comprising: introducing into CD40-bearing cells of the subject, a nucleic acid sequence encoding the protein of this invention, under conditions such that the cells express in the subject an activation inhibiting effective amount of the protein.

In an embodiment of this invention the introducing of the nucleic acid into cells of the subject comprises: a) treating cells of the subject ex vivo to insert the nucleic acid sequence into the cells; and b) introducing the cells from step a) into the subject.

The subject which can be treated by the above-described methods is an animal. Preferably the animal is a mammal. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

This invention provides a method of treating a condition characterized by an unwanted level of CD40-mediated intracellular signaling, in a subject, comprising providing the subject with an amount of an agent capable of inhibiting CD40-mediated intracellular signaling in cells bearing CD40 on the cell surface.

In an embodiment the agent is a protein comprising CRAF1 truncated by from about 323 to about 414 amino acid residues at the amino terminus, or a variant thereof capable of inhibiting CD40-mediated cell activation. In an embodiment the protein is provided by introducing into CD40-bearing cells of the subject, a nucleic acid sequence encoding the protein, under conditions such that the cells express in the subject an activation inhibiting effective amount of the protein.

In an embodiment of this invention the agent is a small molecule. In an embodiment the molecule is modified from a lead inhibitory agent. In an embodiment the agent specifically binds to CD40 intracellular domain.

In an embodiment the condition is organ rejection in a subject receiving transplant organs. Examples of suitable transplant organs include a kidney, heart or liver, as well as others known to those of skill in the art. In another embodiment the condition is an immune response in a subject receiving gene therapy. One difficulty encountered in gene therapy is an immune response by the patient to the gene therapy vector and the proteins it expresses. Because the protein of this invention inhibits the immune response, gene therapy with the protein of this invention does not trigger an immune response. Its immunosuppressant effect also makes it useful as an adjunct to other forms of gene therapy. For example, at the same time that a vector being administered to provide a gene therapy patient with a desired gene product, the patient is also administered a vector which provides the protein of this invention.

In another embodiment the condition is a CD40-dependent immune response. In a specific embodiment the CD40-dependent immune response is an autoimmune response in a subject suffering from an autoimmune disease, including but not limited to rheumatoid arthritis, Myasthenia gravis, systemic lupus erythematosus, Graves' disease, idiopathic thrombocytopenia purpura, hemolytic anemia, diabetes mellitus, a drug-induced autoimmune disease such as drug-induced lupus, psoriasis, or hyper IgE syndrome.

In another embodiment the condition is an allergic response, including but not limited to hay fever or a penicillin allergy.

In an embodiment of this invention the immune response comprises induction of CD23, CD80 upregulation, or rescue from CD95-mediated apoptosis. Because CD40, which is expressed by many tumors, is involved in rescuing cells from apoptosis, inhibitors of CD40-mediated activity are useful as adjunctive agents in chemotherapy.

In an embodiment of this invention the immune response is autoimmune manifestations of an infectious disease. In more specific embodiments the autoimmune manifestations are derived from Reiter's syndrome, spondyloarthritis, Lyme disease, HIV infections, syphilis or tuberculosis.

In an embodiment the condition is dependent on CD40 ligand-induced activation of fibroblast cells, for example arthritis, scleroderma, and fibrosis. In more specific embodiments the arthritis is rheumatoid arthritis, non-rheumatoid inflammatory arthritis, arthritis associated with Lyme disease, or osteoarthritis. In another specific embodiment the fibrosis is pulmonary fibrosis, hypersensitivity pulmonary fibrosis, or a pneumoconiosis. Examples of pulmonary fibrosis include pulmonary fibrosis secondary to adult respiratory distress syndrome, drug-induced pulmonary fibrosis, idiopathic pulmonary fibrosis, or hypersensitivity pneumonitis. Examples of pneumoconiosis include asbestosis, siliconosis, or Farmer's lung. In another specific embodiment the fibrosis is a fibrotic disease of the liver or lung, including fibrotic disease of the lung caused by rheumatoid arthritis or scleroderma, and fibrotic diseases of the liver selected from the group consisting of: Hepatitis-C; Hepatitis-B; cirrhosis; cirrhosis of the liver secondary to a toxic insult; cirrhosis of the liver secondary to drugs; cirrhosis of the liver secondary to a viral infection; and cirrhosis of the liver secondary to an autoimmune disease. In a specific embodiment the toxic insult is alcohol consumption. In another specific embodiment the viral infection is Hepatitis B, Hepatitis C, or hepatitis non-B non-C. In another specific embodiment the autoimmune disease is primary biliary cirrhosis, or Lupoid hepatitis.

In an embodiment of this method the condition is dependent on CD40 ligand-induced activation of endothelial cells. In specific embodiments the condition dependent on CD40 ligand-induced activation of endothelial cells is selected from the group consisting of atherosclerosis, reperfusion injury, allograft rejection, organ rejection, and chronic inflammatory autoimmune diseases. In a more specific embodiment the atherosclerosis is accelerated atherosclerosis associated with organ transplantation. In another specific embodiment the chronic inflammatory autoimmune disease is vasculitis, rheumatoid arthritis, scleroderma, or multiple sclerosis.

In an embodiment the condition is dependent on CD40 ligand-induced activation of epithelial cells. In a specific embodiment the epithelial cells are keratinocytes, and the condition is psoriasis. In another specific embodiment the condition is an inflammatory kidney disease, including inflammatory kidney disease not initiated by autoantibody deposition in kidney and kidney disease which is initiated by autoantibody deposition. In specific embodiments the kidney disease is selected from the group consisting of: membranous glomerulonephritis; minimal change disease/acute tubular necrosis; pauci-immune glomerulonephritis; focal segmental glomerulosclerosis; interstitial nephritis; antitissue antibody-induced glomerular injury; circulating immune-complex disease; a glomerulopathy associated with a multisystem disease; and drug-induced glomerular disease. In an embodiment the antitissue antibody-induced glomerular injury is anti-basement membrane antibody disease. In another embodiment the circulating immune-complex disease is selected from the group consisting of: infective endocarditis; leprosy; syphilis; hepatitis B; malaria; and a disease associated with an endogenous antigen. In a more specific embodiment the endogenous antigen is DNA, thyroglobulin, an autologous immunoglobulin, erythrocyte stroma, a renal tubule antigen, a tumor-specific antigen, or a tumor-associated antigen. In another embodiment the glomerulopathy associated with a multisystem disease is selected from the group consisting of: diabetic nephropathy; systemic lupus erythematosus; Goodpasture's disease; Henoch-Schönlein purpura; polyarteritis; Wegener's granulomatosis; cryoimmunoglobulinemia; multiple myeloma; Waldenstrom's macroglobulinemia; and amyloidosis. In an embodiment the pauci-immune glomerulonephritis is ANCA+ pauci-immune glomerulonephritis, or Wegener's granulomatosis. In an embodiment the interstitial nephritis is drug-induced interstitial nephritis. In another embodiment the kidney disease affects renal tubules, including but not limited to: a kidney disease associated with a toxin; a neoplasia; hypersensitivity nephropathy; Sjögren's syndrome; and AIDS.

In an embodiment the condition is a smooth muscle cell-dependent disease. Examples include vascular diseases such as atherosclerosis; gastrointestinal diseases such as esophageal dysmotility, inflammatory bowel disease, and scleroderma; and bladder diseases.

In an embodiment of this method, the condition is associated with Epstein-Barr virus. Examples of Epstein-Barr virus-associated conditions include mononucleosis, B cell tumors (particularly in immunosuppressed individuals such as chemotherapy patients and those with acquired immune deficiency syndrome (AIDS)), Burkitt's lymphoma, and nasopharyngeal carcinoma. Epstein-Barr virus (EBV) transforms cells using latent infection membrane protein 1 (LMP1). LMP1 binds to CRAF1 (also known as LAP1)(33).

This invention provides a nucleic acid molecule encoding the protein of this invention. The nucleic acid may be DNA (including cDNA) or RNA. It may be single or double stranded, linear or circular. It may be in the form of a vector, such as a plasmid or viral vector, which comprises the nucleic acid molecule operably linked to a transcriptional control sequence recognized by a host cell transformed with the vector.

This invention provides a method of identifying an agent capable of inhibiting CD40-mediated intracellular signaling in a cell expressing CD40 on the cell surface, comprising providing the cell with the agent under conditions permitting activation of the cell in the absence of the agent, and determining decreased or absent activation, thereby identifying an agent capable of inhibiting CD40-mediated intracellular signaling in a cell expressing CD40 on the cell surface. In an embodiment the activation comprises up-regulation of CD23. In an embodiment the conditions permitting activation of the cell comprises contacting the cell with CD40 ligand or portion thereof effective to activate the cell.

This invention will be better understood from the Experimental Details which follow. However, one skilled in the art will readily appreciate that the specific methods and results discussed are merely illustrative of the invention as described more fully in the claims which follow thereafter.
Experimental Details
Activity of N-terminal Truncated CRAF1

The yeast two-hybrid system was used to identify complementary DNAs (cDNAs) encoding protein domains that can bind to the tail. The bait for the yeast two-hybrid screen was a LexA fusion protein containing the cytoplasmic tail of the mouse CD40 receptor (from residue 219 to the COOH-terminus).

The cDNA library for the yeast two-hybrid screen was a mixture of oligo(dT) and random primed cDNAs constructed into the yeast expression vector YSD, which is a centromere-based, galactose-induced yeast expression vector containing the VP16 transcription activation domain. Half of the mRNA used for cDNA synthesis was isolated from uninduced 70Z cells, and the other half was from 70Z cells that were induced with lipopolysaccharide for 12 hours. The primary library contained about $8 \times 10^5$ individual clones, with an average insert size of 0.9 kb. From $2 \times 10^6$ clones of the murine 70Z pre-B cell cDNA library, one (C26) was isolated that met all specificity criteria for binding to the cytoplasmic tail of CD40 in yeast. The C26 CDNA fragment was sequenced and no identical gene was evident in the databases. This gene is called CRAF1 for CD40 receptor-associated factor 1. By Northern (RNA) blot analysis, CRAF1 was expressed in B cell lines representing different stages of B cell differentiation; in addition, it was expressed in all murine tissues examined, including brain, heart, lung, liver, kidney, muscle, small intestine, spleen, and thymus (18).

Mouse and human cDNA libraries were screened to isolate cDNA clones encoding the entire open reading frame of a murine 567-amino acid and a human 568-amino acid protein. The two sequences share 96% identity, with the differences concentrated near the $NH_2$-terminus, indicating that CRAF1 is evolutionarily conserved, particularly in its COOH-terminal 400 amino acids (FIG. 1). The CRAF1 sequence is similar to that of TNF-α receptor-associated factors 1 and 2 (TRAF1 and TRAF2), which can complex with the cytoplasmic tail of TNF-α receptor II (TNFαRII) (19). The COOH-terminus of CRAF1 is related by sequence to each of these TRAF proteins for 150 amino acids, wherein CRAF1 is 59 and 62% identical to TRAF1 or TRAF2, respectively (FIG. 2) (19). This homology subdivides what was termed the "TRAF domain," excluding a more $NH_2$-terminal putative coiled-coiled subdomain (TRAF-N) with which CRAF1 shares only 16 or 12% homology and defines a "TRAF-C" (for COOH-terminal) domain. Because the extracellular domains of CD40 and TNFαRII are homologous, as are their ligands, these data suggest that they may make use of related but distinct signaling molecules. However, the cytoplasmic domains of CD40 and TNFαRII contain no apparent sequence homology, which suggests that the particular contacts involved in binding the signaling molecules to the receptors have diverged.

In addition to the TRAF-C domain, sequence analysis of the CRAF1 protein revealed three potential domains: an amphipathic helix, a string of Zn fingers, and a Zn ring finger domain (FIG. 2A). A helical wheel representation of the putative helix (FIG. 2B) shows that isoleucine (or occasionally leucine) repeats every seven residues through eight consecutive repeats, which implies the presence of an isoleucine zipper in analogy to the leucine zipper seen in other proteins (20). The wheel also indicates that the position next to the zipper is always hydrophobic or uncharged, whereas the other positions around the wheel include multiple charged residues and few hydrophobic ones. This strongly suggests an amphipathic structure that could be an interaction site for another such helix.

Figure 2C:
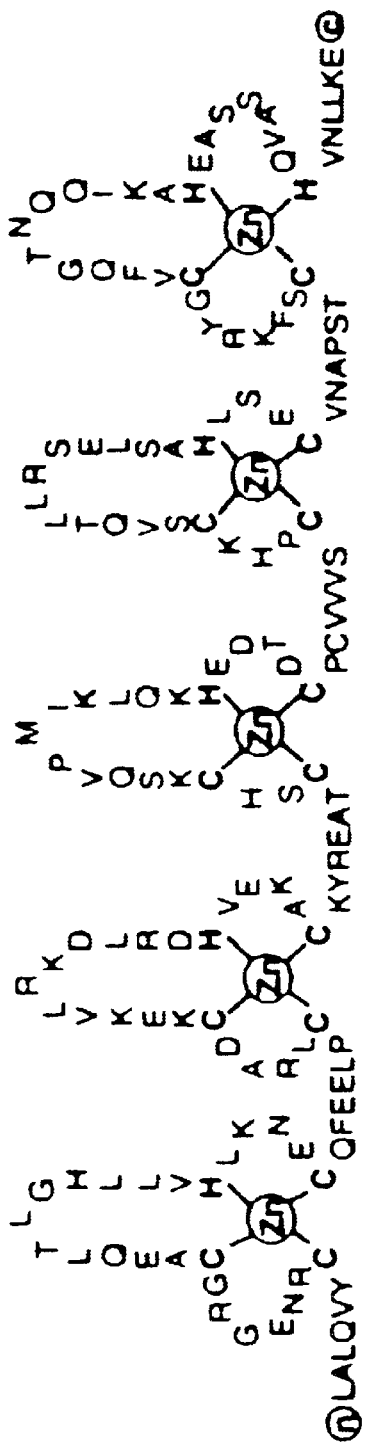

The are five repeats of potential Zn fingers just $NH_2$-terminal to the isoleucine repeats (FIG. 2C). However, the four amino acids that would contact the metal are arranged in the unique pattern Cys—$X_{2-6}$—Cys—$X_{11,12}$—His—$X_{3-7}$ —Cys(His), instead of Cys—$X_{2-4}$—Cys—$X_{12,13}$—His—$X_{2-4}$—His, which is seen in classic Zn fingers (21). At the COOH-terminal edge of finger 2 is a sequence (KACKYR) (SEQ ID NO:5) that could bind to DNA, which suggests that CRAF1 might be a DNA binding protein. The TRAF2 protein contains five fingers with the same pattern of repeats seen in the CRAF1 protein but with weak overall similarity (FIG. 2A), suggesting that these structural units may represent a subclass of Zn finger motifs in this type of signaling molecule. In addition, a Zn ring structure was also evident in the $NH_2$-terminus of CRAF1 (FIG. 2D) (23). This ring motif has been recognized in over 40 proteins that have diverse functions related to DNA mechanics, including recombination, repair, and transcription regulation (24). These structural data suggest that CRAF1 directly transmits CD40 signals to the nucleus.

To further map the region of CRAF1 that interacts with the CD40 cytoplasmic tail, four deletion mutants of the C26 cDNA were generated and studied in the yeast system for their ability to bind to the CD40 cytoplasmic tail. The TRAF-C subdomain of CRAF1 was necessary and sufficient for CRAF1 to interact with CD40 (FIG. 3). Moreover, the CRAF1 protein in yeast could interact with itself, forming homodimers or oligomers, also mediated by the TRAF-C domain (FIG. 3). Quantitative analysis of β-galactosidase expression indicated that the affinity of the TRAF-C domain of CRAF1 to bind to CD40 and to dimerize with itself was not increased by addition of the rest of the TRAF domain. These data suggest that the COOH-terminal portion of the TRAF domain functions as an individual unit (the TRAF-C domain) that is involved in both binding to the receptor tail and mediating dimerization.

Overexpression of the C26 partial cDNA fragment acts as a dominant negative protein, inhibiting CD40 signaling presumably by prevention of the binding of the endogenous protein to the CD40 tail. Ramos 2G6 cells (25) can be induced to up-regulate surface CD23 molecules in a contact-dependent fashion that depends on CD40L interaction with CD40 (3). Therefore, a cDNA construct was generated that drives the expression of a polyhistidine/C26 fusion protein (pEBVHis/C26) in mammalian cells. The C26 cDNA fragment was cut with Eco RI-Hinc III from yeast vector YSD, ligated into Bluescript IISK+(Stratagene), and then recloned in-frame into the pEBVHisA vector (Invitrogen), with the use of Bam H1 and Kpn 1 cuts, to create pEBVHis/C26. Stable Ramos cell lines containing either this construct or the control construct (pEBVHis/lacZ) were isolated by electroporation and hygromycin selection.

Figure 4A:
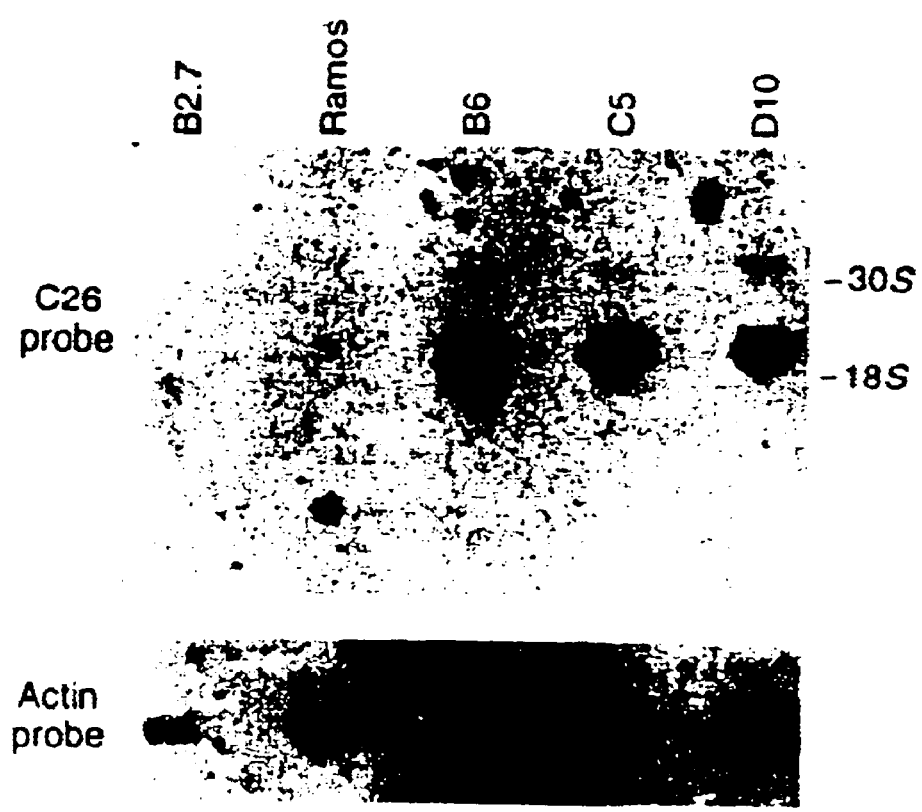

As a negative control for the effects of C26, the β-galactosidase gene was expressed as a fusion protein in the same vector (pEB-VHis/lacZ) (Invitrogen). These constructs were electroporated into Ramos 2G6 cells, and clones expressing a large amount of pE-BVHis/C26 mRNA were prepared (FIG. 4A). CD40L-expressing cells (293.CD40L) were then cultured with Ramos 2G6 cells that either were not transfected or were stably expressing pEBVHis/lacZ or pEBVHis/C26. Either $2\times10^5$ Ramos B cells or Ramos B cells transfected with pEBVHis/C26 or pEBVHis/lacZ were incubated for 18 to 24 hours in 0.2 ml of medium alone, in rIL-4 at a concentration of 25 ng/ml, or in the presence of $5\times10^4$ 293.CD40L cells. In some cases, mAb 5C8 (anti-CD40L) was added. Cells were then washed and incubated with saturating concentrations of mAb Leu-16 (anti-CD20) conjugated to fluorescein isothiocyanate (Becton Dickinson) and mAb to CD23 conjugated to phycoerythrin (Biosource International) for 45 min at 4° C. in the presence of heat-aggregated IgG (80 µg/ml) (International Enzyme). Cells were washed to remove unbound antibody before fluorescence intensity was measured on a FACSCAN cytofluorograph (Becton Dickinson) with Consort 30 software.

The control and pEBVHis/lacZ-transfected Ramos lines up-regulated CD23; this effect was inhibited by a monoclonal antibody (mAb) to CD40L (mAb 5C8). In contrast, the ability of the pEBVHis/C26 transfectants to up-regulate CD23 in response to CD40L-CD40 signals was diminished. The inhibition of CD23 up-regulation by pEB-VHis/C26 was relatively specific because recombinant interleukin-4 (rIL-4)-induced up-regulation of CD23 was not affected (FIG. 4B-M). Similar effects were seen in all three subclones of pEBVHis/C26 transfectants. Thus, the COOH-terminal region of CRAF1 represented in the C26 cDNA could block the CD40 triggering of Ramos cells.

CD40 is a type I transmembrane glycoprotein belonging to the TNF receptor superfamily. Besides CD40, 11 other proteins have been identified in this superfamily, which includes TNF receptors I and II, the nerve growth factor (NGF) receptor, and Fas (28). Members within this family share sequence similarity through their extracellular regions that contain multiple cysteine-rich pseudorepeats. The common structural framework of the extracellular domain is reflected in the ability of the TNF receptor superfamily members to interact with a parallel family of TNF-related cytokine ligands. Eight such ligands (including TNF-α, CD40L, and FasL) have been cloned that share extensive sequence identity and exist as secreted cytokines or type II transmembrane ligands (28).

The functions of TNF receptor superfamily members are very divergent. They range from general acute phase response and lymphocyte activation to nerve cell growth. In some circumstances, they have opposite roles. For instance, Fas and TNFαRI can cause apoptosis upon ligand stimulation, whereas CD40 and NGF receptors can rescue cells from apoptosis (29). In addition, stimulation of either TNFαRI, TNFαRII, or CD40 receptor activates nuclear factor kappa B (30). Because CRAF1 is very similar to TRAF1 and TRAF2, a family of signal transduction proteins (the TRAF family) probably exists as downstream signal transducers of the TNF receptor superfamily. It is likely that direct binding between members of the TNF receptor family and the TRAF family will be specific because the cytoplasmic tails of these TNF receptor superfamily members are relatively short and show little or no sequence homology. Consistent with this notion, the COOH-terminal segment of CRAF1 does not interact with the tail of Fas or with TNFαRII (FIG. 3). However, the fact that the members of the TRAF family can form either homodimers or heterodimers could result in extensive diversity and specificity in their signal transduction pathways. It is even possible that apoptosis and cell survive may be determined by an equilibrium of dimerization between TRAF family members.

The functional consequences of CD40 signaling are different for B cells at different stages of differentiation (31). CD40 crosslinking causes resting B cells to enter into the cells cycle, enhancing the proliferative rate of some chronic lymphocytic leukemia B cells, induces some B lymphoma cells to apoptose, and prevents germinal center B cells from apoptosis (14). However, CRAF1 is expressed at all stages of B cell differentiation and may be ubiquitous.

Gene Therapy

The invention features expression vectors for in vivo transfection and expression in particular cell types of CD40 receptor-associated factor truncated at the amino terminus so as to antagonize the function of wild type CD40 receptor-associated factor in an environment in which the wild-type protein is expressed (i.e., introduce abnormal CD40 receptor-associated factor that acts as a dominant negative protein to inhibit CD40 signaling).

Expression constructs of CD40 receptor-associated factor polypeptides may be administered in any biologically effective carrier that is capable of effectively delivering a polynucleotide sequence encoding the CD40 receptor-associated factor to cells in vivo. Approaches include insertion of the subject gene in viral vectors including recombinant retroviruses, adenovirus, adeno-associated virus and herpes simplex virus-1, or recombinant bacterial or eukaryotic plasmids. Viral vectors transfect cells directly, plasmid DNA can be delivered with the help of, for example, cationic liposomes or derivatized (e.g., antibody conjugated) polylysine conjugates, gramacidin S, artificial viral envelopes or other such intracellular carriers, as well as direct injection of the gene construct or $CaPO_4$ precipitation carried out in vivo.

Any of the methods known in the art for the insertion of polynucleotide sequences into a vector may be used. See, for example, Sambrook et al., Molecular Cloning: A Laboratory Manual, Cold Spring Harbor Laboratory, Cold Spring Harbor, NY (1989) and Ausubel et al., Current Protocols in Molecular Biology, J. Wiley & Sons, NY (1992), both of which are incorporated herein by reference. Conventional vectors consist of appropriate transcriptional/translational control signals operatively linked to the polynucleotide sequence for a particular anti-fibrotic polynucleotide sequence Promoters/enhancers may also be used to control expression of anti-fibrotic polypeptide. Promoter activation may be tissue specific or inducible by a metabolic product or administered substance. Such promoters/enhancers include, but are not limited to, the native E2F promoter, the cytomegalovirus immediate-early promoter/enhancer (Karasuyama et al., *J. Exp. Med*., 169: 13 (1989)); the human beta-actin promoter (Gunning et al., *Proc. Natl. Acad. Sci. USA*, 84: 4831 (1987); the glucocorticoid-inducible promoter present in the mouse mammary tumor virus long terminal repeat (MMTV LTR) (Klessig et al., *Mol. Cell. Biol*., 4: 1354 (1984)); the long terminal repeat sequences of Moloney murine leukemia virus (MuLV LTR) (Weiss et al., RNA Tumor Viruses, Cold Spring Harbor Laboratory, Cold Spring Harbor, N.Y. (1985)); the SV40 early region promoter (Bernoist and Chambon, *Nature*, 290:304 (1981)); the promoter of the Rous sarcoma virus (RSV) (Yamamoto et al., *Cell*, 22:787 (1980)); the herpes simplex virus (HSV) thymidine kinase promoter (Wagner et al., *Proc. Natl. Acad. Sci. USA*, 78: 1441 (1981)); the adenovirus promoter (Yamada et al., *Proc. Natl. Acad. Sci. USA*, 82: 3567 (1985)).

Expression vectors compatible with mammalian host cells for use in gene therapy of tumor cells include, for example, plasmids; avian, murine and human retroviral vectors; adenovirus vectors; herpes viral vectors; and non-replicative pox viruses. In particular, replication-defective recombinant viruses can be generated in packaging cell lines that produce only replication-defective viruses. See Current Protocols in Molecular Biology: Sections 9.10–9.14 (Ausubel et al., eds.), Greene Publishing Associcates, 1989.

Specific viral vectors for use in gene transfer systems are now well established. See for example: Madzak et al., *J. Gen. Virol*., 73: 1533–36 (1992: papovavirus SV40); Berkner et al., *Curr. Top. Microbiol. Immunol*., 158: 39–61 (1992: adenovirus); Moss et al., *Curr. Top. Microbiol. Immunol*., 158: 25–38 (1992: vaccinia virus); Muzyczka, *Curr. Top. Microbiol. Immunol*., 158: 97–123 (1992: adeno-associated virus); Margulskee, *Curr. Top. Microbiol. Immunol*., 158: 67–93 (1992: herpes simplex virus (HSV) and Epstein-Barr virus (HBV)); Miller, Curr. *Top. Microbiol. Immunol*., 158: 1–24 (1992:retrovirus); Brandyopadhyay et al., *Mol. Cell. Biol*., 4: 749–754 (1984: retrovirus); Miller et al., *Nature*, 357: 455–450 (1992: retrovirus); Anderson, *Science*, 256: 808–813 (1992:retrovirus), all of which are incorporated herein by reference.

Preferred vectors are DNA viruses that include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., *Gene Therapy* 1: 367–384, 1994; U.S. Pat. Nos. 4,797,368 and 5,399,346 and discussion below.

Furthermore, abnormal or wild-type CD40 receptor-associated factor may also be introduced into a target cell using a variety of well-known methods that use non-viral based strategies that include electroporation, membrane fusion with liposomes, high velocity bombardment with DNA-coated microprojectiles, incubation with calcium-phosphate-DNA precipitate, DEAE-dextran mediated transfection, and direct micro-injection into single cells. For instance, an anti-fibrotic polynucleotide encoding an immunosuppressant effective amount of an abnormal CD40 receptor-associated factor may be introduced into a cell by calcium phosphate coprecipitation (Pillicer et al., *Science*, 209: 1414–1422 (1980); mechanical microinjection and/or particle acceleration (Anderson et al., *Proc. Natl. Acad. Sci. USA*, 77: 5399–5403 (1980); liposome based DNA transfer (e.g., LIPOFECTIN-mediated transfection Fefgner et al., *Proc. Natl. Acad. Sci. USA*, 84: 471–477 (1987), Gao and *Huang, Biochem. Biophys. Res. Comm*., 179: 280–285, 1991); DEAE Dextran-mediated transfection; electroporation (U.S. Pat. No. 4,956,288); or polylysine-based methods in which DNA is conjugated to deliver DNA preferentially to liver hepatocytes (Wolff et al., *Science*, 247: 465–468 (1990), Curiel et al., *Human Gene Therapy* 3: 147–154 (1992). Each of these methods is well represented in the art. Moreover, plasmids containing isolated polynucleotide sequences encoding CD40 receptor-associated factor polypeptide may placed into cells using many of these same methods.

CD40 receptor-associated factor itself may also be chemically modified to facilitate its delivery to a target cell. One such modification involves increasing the lipophilicity of the CD40 receptor-associated factor in order to increase cell surface binding and stimulate non-specific endocytosis of the polypeptide. A wide variety of lipopeptides, fatty acids, and basic polymers (e.g., tripalmitoyl-S-glycerylcysteil-seryl-serine; palmitic acid; polyarginine) may be linked to an anti-fibrotic polypeptide to accomplish this. See U.S. Pat. No. 5, 219,990, incorporated herein by reference.

Delivery may also be effected by using carrier moieties known to cross cell membranes. For example, an abnormal CD40 receptor-associated factor may be fused to a carrier moiety, preferably by genetic fusion, and the fused construct may be expressed in bacteria or yeast using standard techniques. Thus, polynucleotide sequences encoding abnormal or wild type CD40 receptor-associated factor useful in the present invention, operatively linked to regulatory sequences, may be constructed and introduced into appropriate expression systems using conventional recombinant DNA techniques. The resulting fusion protein may then be purified and tested for its capacity to enter intact target cells and inhibit growth of the target cells once inside the target. For example, recombinant methods may be used to attach a carrier moiety to anti-fibrotic polynucleotide sequences by joining the polynucleotide sequence encoding for abnormal CD40 receptor-associated factor with the polynucleotide sequence encoding a carrier moiety and introducing the resulting construct into a cell capable of expressing the conjugate. Two separate sequences may be synthesized, either by recombinant means or chemically, and subsequently joined using known methods. The entire conjugate may be chemically synthesized as a single amino acid sequence.

Useful carrier moieties include, for example, bacterial hemolysins or "blending agents" such as alamethicin or sulfhydryl activated lysins. Other carrier moieties include cell entry components of bacterial toxins such as Pseudomonas exotoxin, tetanus toxin, ricin toxin and diphtheria toxin. Other useful carrier moieties include proteins which are viral receptors, cell receptors or cell ligands for specific receptors that are internalized and cross mammalian cell membranes via specific interaction with cell surface receptors. Such cell ligands include epidermal growth factor, fibroblast growth factor, transferrin and platelet derived growth factor. The carrier moiety may also include bacterial immunogens, parasitic immunogens, viral immunogens, immunoglobulins, and cytokines.

In one embodiment, purified human immunodeficiency virus type-1 (HIV) tat protein is the carrier moiety. Purified human immunodeficiency virus type-1 (HIV) tat protein is taken up from the surrounding medium by human cells growing in culture. See Frankel et al., *Cell* 55: 1189–1193, (1988); Fawell et al., *Proc. Natl. Acad. Sci. USA*, 91: 664–668 (1994) (use of tat conjugate); and Pepinsky et al., *DNA and Cell Biology*, 13: 1011–1019 (1994) (use of tat genetic fusion construct), all of which are incorporated herein by reference. See also PCT Application Ser. No. PCT/US93/07833, published 3 Mar. 1994 which describes the tat-mediated uptake of the papillomavirus E2 repressor; utilizing a fusion gene in which the HIV-1 tat gene is linked to the carboxy-terminal region of the E2 repressor open reading frame. The tat protein can deliver, for example, abnormal or wild type CD40 receptor-associated factor and polynucleotide sequences into cells, either in vitro or in vivo. For example, delivery can be carried out in vitro by adding a genetic fusion encoding an abnormal CD40 receptor-associated factor- tat conjugate to cultured cells to produce cells that synthesize the tat conjugate or by combining a sample (e.g., blood, bone marrow, tumor cell) from an individual directly with the conjugate, under appropriate conditions. The target cells may be in vitro cells such as cultured animal cells, human cells or microorganisms. Delivery may be carried out in vivo by administering the CD40 receptor-associated factor and tat protein to an individual in which it is to be used. The target may be in vivo cells, i.e., cells composing the organs or tissue of living animals or humans, or microorganisms found in living animals or humans. The ADP ribosylation domain from Pseudomonas exotoxin ("PE") and pancreatic ribonuclease have been conjugated to tat to confirm cytoplasmic delivery of a protein. The ADP phosphorylation domain is incapable of entering cells so that cytoplasmic delivery of this molecule would be confirmed if cell death occurs. Likewise, ribonuclease itself is incapable of entering cells so that inhibition of protein synthesis would be a hallmark of intracellular delivery using a tat conjugate.

Chemical (i.e., non-recombinant) attachment of CD40 receptor-associated factor polypeptide sequences to a carrier moiety may be effected by any means which produces a link between the two components which can withstand the conditions used and which does not alter the function of either component. Many chemical cross-linking agents are known and may be used to join an abnormal or wild-type CD40 receptor-associated factor polynucleotide sequence or polypeptide to carrier moieties. Among the many intermolecular cross-linking agents are, for example, succinimidyl 3-(2-pyridyldithio)propionate (SPDP) or N, N'-(1,2-phenylene)bismaleimide are highly specific for sulfhydryl groups and form irreversible linkages; N, N'-ethylene-bis-(iodoacetamide) (specific for sulfhydryl); and 1,5-difluoro-2,4-dinitrobenzene (forming irreversible linkages with tyrosine and amino groups). Other agents include p,p'-difluoro-m,m'-dinitrodiphenylsulfone (forming irreversible linkages with amino and phenolic groups); dimethyl adipimidate (specific for amino groups); hexamethylenediisocyanate (specific for amino groups); disdiazobenzidine (specific for tyrosine and histidine); succinimidyl 4-(N-maleimidomethyl)cyclohexane-1-carboxylate (SMCC); m-maleimidobenzoyl-N-hydroxysuccinimide ester (MBS); and succinimide 4-(p-maleimidophenyl)butyrate (SMPB). The succinimidyl group of these cross-linkers reacts with a primary amine, and the thiol-reactive maleimide reacts with the thiol of a cysteine residue. See, Means and Feeney, Chemical Modification of Proteins, Holden-Day, 39–43, 1974; and S.S. Wong, Chemistry of Protein Conjugation and Cross-Linking, CRC Press, 1971. All the cross-linking agents discussed herein are commercially available and detailed instructions for their use are available from the suppliers.

In clinical settings, the delivery systems for the abnormal or wild-type CD40 receptor-associated factor polynucleotide sequence can be introduced into a patient by any number of methods, each of which is familiar to persons of ordinary skill. Specific incorporation of the delivery system in the target cells occurs primarily from specificity of transfection provided by the gene delivery vehicle, cell type or tissue type expression due to the transcriptional regulatory sequences controlling expression of the polynucleotide, or a combination thereof. In other embodiments, initial delivery of the recombinant gene is more limited with introduction into the animal being localized by, for example, catheter (U.S. Pat. No. 5,328,470) or stereotactic injection (Chen et al., *Proc. Natl. Acad. Sci. USA*, 91: 3054–3057 (1994).

The pharmaceutical preparation of the gene therapy construct can consist essentially of the gene delivery system in an acceptable diluent, or can comprise a slow release matrix in which the gene delivery vehicle is embedded. Where the complete gene delivery system can be produced intact from recombinant cells such as retroviral vectors, the pharmaceutical preparation can include one or more cells which produce the gene delivery system.

Effective amounts of the compounds of the invention may be administered in any manner which is medically acceptable. The method of administration may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, topical, or inhaled. The term "pharmaceutically acceptable carrier" means one or more organic or inorganic ingredients, natural or synthetic, with which the molecule is combined to facilitate its application. A suitable carrier includes sterile saline although other aqueous and non-aqueous isotonic sterile solutions and sterile suspensions known to be pharmaceutically acceptable are known to those of ordinary skill in the art. In this regard, the term "carrier" encompasses liposomes or the HIV-1 tat protein (See Pepinsky et al., supra) as well as any plasmid and viral expression vectors. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

In preferred methods, an effective amount of the abnormal or wild-type CD40 receptor-associated factor or polynucleotide sequence encoding the factor (contained within its attendant vector; i.e., "carrier) may be directly administered to a target cell or tissue via direct injection with a needle or via a catheter of other delivery tube placed into the cell or tissue. Dosages will depend primarily on factors such as the condition being treated, the selected polynucleotide, the age, weight, and health of the subject, and may thus vary among subjects. An effective amount for a human subject is believed to be in the range of about 0.1 to about 50 ml of saline solution containing from about $1 \times 10^7$ to about $1 \times 10^{11}$ plaque forming units (pfu)/ml CD40 receptor-associated factor polynucleotide containing, viral expression vectors.

Target cells treated by abnormal or wild-type CD40 receptor-associated factor polynucleotide sequences may be administered topically, intraocularly, parenterally, intranasally, intratracheal, intrabronchially, intramuscularly, subcutaneously or by any other means. Target cells to be treated by abnormal or wild-type CD40 receptor-associated factor protein may be administered topically, intraocularly, parenterally, intranasally, intratracheal, intrabronchially, intramuscularly, subcutaneously or by any other means.

The protein compounds of the invention are administered at any dose per body weight and any dosage frequency which is medically acceptable. Acceptable dosage includes a range of between about 0.01 and 500 mg/kg subject body weight. A preferred dosage range is between about 1 and 100 mg/kg. Particularly preferred is a dose of between about 1 and 30 mg/kg. The dosage is repeated at intervals ranging from each day to every other month. One preferred dosing regime is to administer a compound of the invention daily for the first three days of treatment, after which the compound is administered every 3 weeks, with each administration being intravenously at 5 or 10 mg/kg body weight. Another preferred regime is to administer a compound of the invention daily intravenously at 5 mg/kg body weight for the first three days of treatment, after which the compound is administered subcutaneously or intramuscularly every week at 10 mg per subject.

The protein compounds of the invention, similarly to the therapeutic nucleotide sequences, may be delivered to tissues in a liposome-encapsulated formulation, or conjugated to carrier moieties such as IIIV tat protein. This delivery can be systemic, such as by intravascular delivery, or local. Local means of delivery of liposome-encapsulated compounds of the invention include intratumor or intraorgan injection. It also includes local delivery by catheter, such as intrahepatic delivery into the portal vein, intrarenal or intraprostate delivery via the urethra, intracholecystic delivery via the bile duct, or delivery into various blood vessels of interest, particularly the coronary vessels or sites of vascular stenosis. Targeted delivery may be accomplished by inserting components into the surface of the liposomes or other carrier moieties which confer target specificity. For example, areas of inflammation might be targeted by coating the carrier liposomes with monoclonal antibodies specific for anti-CD40 ligand. Various types of tumors could be selectively targeted by coating liposomes with monoclonal antibodies specific for surface antigens characteristic of the tumor cells.

The compounds of the invention may be administered as a single dosage for certain indications such as preventing immune response to an antigen to which a subject is exposed for a brief time, such as an exogenous antigen administered on a single day of treatment Examples of such an antigen would include coadministration of a compound of the invention along with a gene therapy vector, or a therapeutic agent such as an antigenic pharmaceutical or a blood product. In indications where antigen is chronically present, such as in controlling immune reaction to transplanted tissue or to chronically administered antigenic pharmaceuticals, the compounds of the invention are administered at intervals for as long a time as medically indicated, ranging from days or weeks to the life of the subject.

What is claimed is:

1. An isolated protein consisting of amino acids 416–568 of SEQ ID NO:2.

2. An isolated protein consisting of amino acids 415–567 of SEQ ID NO:1.

* * * * *

SEQUENCE LISTING

```
<160> NUMBER OF SEQ ID NOS: 11

<210> SEQ ID NO 1
<211> LENGTH: 567
<212> TYPE: PRT
<213> ORGANISM: Mouse Sp.

<400> SEQUENCE: 1

Met Glu Ser Ser Lys Lys Met Asp Ala Ala Gly Thr Leu Gln Pro Asn
1               5                   10                  15

Pro Pro Leu Lys Leu Gln Pro Asp Arg Gly Ala Gly Ser Val Leu Val
            20                  25                  30

Pro Glu Gln Gly Gly Tyr Lys Glu Lys Phe Val Lys Thr Val Glu Asp
        35                  40                  45

Lys Tyr Lys Cys Glu Lys Cys Arg Leu Val Leu Cys Asn Pro Lys Gln
    50                  55                  60

Thr Glu Cys Gly His Arg Phe Cys Glu Ser Cys Met Ala Ala Leu Leu
```

-continued

```
             65                  70                  75                  80
Ser Ser Ser Ser Pro Lys Cys Thr Ala Cys Gln Glu Ser Ile Ile Lys
                85                  90                  95

Asp Lys Val Phe Lys Asp Asn Cys Cys Lys Arg Glu Ile Leu Ala Leu
               100                 105                 110

Gln Val Tyr Cys Arg Asn Glu Gly Arg Gly Cys Ala Glu Gln Leu Thr
               115                 120                 125

Leu Gly His Leu Leu Val His Leu Lys Asn Glu Cys Gln Phe Glu Glu
       130                 135                 140

Leu Pro Cys Leu Arg Ala Asp Cys Lys Glu Lys Val Leu Arg Lys Asp
145                 150                 155                 160

Leu Arg Asp His Val Glu Lys Ala Cys Lys Tyr Arg Glu Ala Thr Cys
                   165                 170                 175

Ser His Cys Lys Ser Gln Val Pro Met Ile Lys Leu Gln Lys His Glu
               180                 185                 190

Asp Thr Asp Cys Pro Cys Val Val Ser Cys Pro His Lys Cys Ser
           195                 200                 205

Val Gln Thr Leu Leu Arg Ser Glu Leu Ser Ala His Leu Ser Glu Cys
       210                 215                 220

Val Asn Ala Pro Ser Thr Cys Ser Phe Lys Arg Tyr Gly Cys Val Phe
225                 230                 235                 240

Gln Gly Thr Asn Gln Gln Ile Lys Ala His Glu Ala Ser Ser Ala Val
                   245                 250                 255

Gln His Val Asn Leu Leu Lys Glu Trp Ser Asn Ser Leu Glu Lys Lys
               260                 265                 270

Val Ser Leu Leu Gln Asn Glu Ser Val Glu Lys Asn Lys Ser Ile Gln
       275                 280                 285

Ser Leu His Asn Gln Ile Cys Ser Phe Glu Ile Glu Ile Glu Arg Gln
       290                 295                 300

Lys Glu Met Leu Arg Asn Asn Glu Ser Lys Ile Leu His Leu Gln Arg
305                 310                 315                 320

Val Ile Asp Ser Gln Ala Glu Lys Leu Lys Glu Leu Asp Lys Glu Ile
                   325                 330                 335

Arg Pro Phe Arg Gln Asn Trp Glu Glu Ala Asp Ser Met Lys Ser Ser
               340                 345                 350

Val Glu Ser Leu Gln Asn Arg Val Thr Glu Leu Glu Ser Val Asp Lys
       355                 360                 365

Ser Ala Gly Gln Ala Ala Arg Asn Thr Gly Leu Leu Glu Ser Gln Leu
       370                 375                 380

Ser Arg His Asp Gln Thr Leu Ser Val His Asp Ile Arg Leu Ala Asp
385                 390                 395                 400

Met Asp Leu Arg Phe Gln Val Leu Glu Thr Ala Ser Tyr Asn Gly Val
                   405                 410                 415

Leu Ile Trp Lys Ile Arg Asp Tyr Lys Arg Arg Lys Gln Glu Ala Val
               420                 425                 430

Met Gly Lys Thr Leu Ser Leu Tyr Ser Gln Pro Phe Tyr Thr Gly Tyr
       435                 440                 445

Phe Gly Tyr Lys Met Cys Ala Arg Val Tyr Leu Asn Gly Asp Gly Met
       450                 455                 460

Gly Lys Gly Thr His Leu Ser Leu Phe Phe Val Ile Met Arg Gly Glu
465                 470                 475                 480

Tyr Asp Ala Leu Leu Pro Trp Pro Phe Lys Gln Lys Val Thr Leu Met
                   485                 490                 495
```

```
Leu Met Asp Gln Gly Ser Ser Arg Arg His Leu Gly Asp Ala Phe Lys
            500                 505                 510
Pro Asp Pro Asn Ser Ser Phe Lys Lys Pro Thr Gly Glu Met Asn
        515                 520                 525
Ile Ala Ser Gly Cys Pro Val Phe Val Ala Gln Thr Val Leu Glu Asn
            530                 535                 540
Gly Thr Tyr Ile Lys Asp Asp Thr Ile Phe Ile Lys Val Ile Val Asp
545                 550                 555                 560
Thr Ser Asp Leu Pro Asp Pro
                565
```

<210> SEQ ID NO 2
<211> LENGTH: 568
<212> TYPE: PRT
<213> ORGANISM: Homo Sapiens

<400> SEQUENCE: 2

```
Met Glu Ser Ser Lys Lys Met Asp Ser Pro Gly Ala Leu Gln Thr Asn
1               5                   10                  15
Pro Pro Leu Lys Leu His Thr Asp Arg Ser Ala Gly Thr Pro Val Phe
            20                  25                  30
Val Pro Glu Gln Gly Gly Tyr Lys Glu Lys Phe Val Lys Thr Val Glu
        35                  40                  45
Asp Lys Tyr Lys Cys Glu Lys Cys His Leu Val Leu Cys Ser Pro Lys
    50                  55                  60
Gln Thr Glu Cys Gly His Arg Phe Cys Glu Ser Cys Met Ala Ala Leu
65                  70                  75                  80
Leu Ser Ser Ser Pro Lys Cys Thr Ala Cys Gln Glu Ser Ile Val
                85                  90                  95
Lys Asp Lys Val Phe Lys Asp Asn Cys Cys Lys Arg Glu Ile Leu Ala
            100                 105                 110
Leu Gln Ile Tyr Cys Arg Asn Glu Ser Arg Gly Cys Ala Glu Gln Leu
        115                 120                 125
Thr Leu Gly His Leu Leu Val His Leu Lys Asn Asp Cys His Phe Glu
    130                 135                 140
Glu Leu Pro Cys Val Arg Pro Asp Cys Lys Glu Lys Val Leu Arg Lys
145                 150                 155                 160
Asp Leu Arg Asp His Val Glu Lys Ala Cys Lys Tyr Arg Glu Ala Thr
                165                 170                 175
Cys Ser His Cys Lys Ser Gln Val Pro Met Ile Ala Leu Gln Lys His
            180                 185                 190
Glu Asp Thr Asp Cys Pro Cys Val Val Ser Cys Pro His Lys Cys
        195                 200                 205
Ser Val Gln Thr Leu Leu Arg Ser Glu Leu Ser Ala His Leu Ser Glu
    210                 215                 220
Cys Val Asn Ala Pro Ser Thr Cys Ser Phe Lys Arg Tyr Gly Cys Val
225                 230                 235                 240
Phe Gln Gly Thr Asn Gln Ile Lys Ala His Glu Ala Ser Ser Ala
                245                 250                 255
Val Gln His Val Asn Leu Leu Lys Glu Trp Ser Asn Ser Leu Glu Lys
            260                 265                 270
Lys Val Ser Leu Leu Gln Asn Glu Ser Val Glu Lys Asn Lys Ser Ile
        275                 280                 285
Gln Ser Leu His Asn Gln Ile Cys Ser Phe Glu Ile Glu Ile Glu Arg
```

-continued

```
                        290                     295                     300
Gln Lys Glu Met Leu Arg Asn Asn Glu Ser Lys Ile Leu His Leu Gln
305                     310                     315                     320

Arg Val Ile Asp Ser Gln Ala Glu Lys Leu Lys Glu Leu Asp Lys Glu
                    325                     330                     335

Ile Arg Pro Phe Arg Gln Asn Trp Glu Glu Ala Asp Ser Met Lys Ser
                340                     345                     350

Ser Val Glu Ser Leu Gln Asn Arg Val Thr Glu Leu Glu Ser Val Asp
                355                     360                     365

Lys Ser Ala Gly Gln Val Ala Arg Asn Thr Gly Leu Leu Glu Ser Gln
370                     375                     380

Leu Ser Arg His Asp Gln Met Leu Ser Val His Asp Ile Arg Leu Ala
385                     390                     395                     400

Asp Met Asp Leu Arg Phe Gln Val Leu Glu Thr Ala Ser Tyr Asn Gly
                405                     410                     415

Val Leu Ile Trp Lys Ile Arg Asp Tyr Lys Arg Lys Gln Glu Ala
                420                     425                     430

Val Met Gly Lys Thr Leu Ser Leu Tyr Ser Gln Pro Phe Tyr Thr Gly
                435                     440                     445

Tyr Phe Gly Tyr Lys Met Cys Ala Arg Val Tyr Leu Asn Gly Asp Gly
                450                     455                     460

Met Gly Lys Gly Thr His Leu Ser Leu Phe Phe Val Ile Met Arg Gly
465                     470                     475                     480

Glu Tyr Asp Ala Leu Leu Pro Trp Pro Phe Lys Gln Lys Val Thr Leu
                485                     490                     495

Met Leu Met Asp Gln Gly Ser Ser Arg Arg His Leu Gly Asp Ala Phe
                500                     505                     510

Lys Pro Asp Pro Asn Ser Ser Phe Lys Lys Pro Thr Gly Glu Met
                515                     520                     525

Asn Ile Ala Ser Gly Cys Pro Val Phe Val Ala Gln Thr Val Leu Glu
                530                     535                     540

Asn Gly Thr Tyr Ile Lys Asp Asp Thr Ile Phe Ile Lys Val Ile Val
545                     550                     555                     560

Asp Thr Ser Asp Leu Pro Asp Pro
                565
```

<210> SEQ ID NO 3
<211> LENGTH: 2359
<212> TYPE: DNA
<213> ORGANISM: Mouse Sp.

<400> SEQUENCE: 3

```
ggcggcggag gatgcgcgcg gcgcctgagc cggccgaacg ggcggcctcg gggtacaggg      60
tccccattac ttgaaggata aggctggcac ggctccgacg tctgtgtgga agcttctccc     120
tcccttctga gcttctctag actccttaca gcgcacggca cagaatttca gtttcctaag    180
atggagtcaa gcaaaaagat ggatgctgct ggcacactgc agcctaaccc accctaaag    240
ctgcagcctg atcgcggcgc agggtccgtg ctcgtgccgg agcaaggagg ctacaaggag    300
aagtttgtga agacggtgga agacaagtac aagtgcgaga agtgccgcct ggtgctgtgc    360
aacccgaagc agacggagtg tggccaccgg ttctgcgaga gctgcatggc cgccctgctg    420
agctcctcca gtccaaaatg cacagcgtgc caagaaagca tcatcaaaga caaggtgttt    480
aaggataatt gctgcaagag agagattctg gcccttcagg tctactgtcg gaatgaaggc    540
```

```
agaggttgtg cggagcagct gactctggga catctgctgg tgcacctaaa aaatgaatgt      600
cagtttgagg aacttccctg tctgcgtgcc gactgcaaag aaaaagtact gagaaaagac      660
ttgcgggatc acgtggaaaa ggcctgtaaa taccgcgagg ccacgtgcag tcactgcaag      720
agccaagtgc ccatgatcaa actgcagaaa catgaagaca cagattgtcc ctgtgtggtg      780
gtatcctgcc ctcacaagtg cagcgttcag actcttctaa ggagtgagtt gagtgcacac      840
ttgtccgagt gtgtcaatgc ccccagcacc tgtagtttta agcgctatgg ctgcgttttt      900
cagggtacaa accagcagat caaggcccat gaggccagct ccgcggtaca gcacgtgaac      960
ctgctgaagg agtggagcaa ctccctggag aagaaggttt ccctgctgca gaatgaaagt     1020
gttgagaaaa acaagagcat ccaaagcctg cacaaccaga tctgcagctt tgagatcgag     1080
attgagaggc agaaggagat gctccgaaac aacgagtcca agatccttca cctgcagcgg     1140
gtaatcgaca gccaagcaga gaaactgaaa gaactggaca aggagatccg tcccttccgg     1200
cagaactggg aggaagcgga cagcatgaag agcagtgtgg agtccctcca gaaccgagtg     1260
actgagctgg agagcgtaga caaaagtgcg gggcaggcgg ctcgcaacac aggcttgctg     1320
gagtcccagc tgaccggca tgaccagacg ttgagtgttc atgacatccg cttggccgac     1380
atggacctgc ggttccaggt cctcgagacc gccagctaca cgggtgctg atctggaag       1440 atccgtgact acaagcgccg gaagcaggag ccgtcatgg ggaagaccct gtctctctac       1500
agccagcctt tctacacagg ttattttggc tataagatgt gtgccagggt ctacctgaat     1560
ggggacggaa tggggaaagg gacacacttg tcgctgtttt ttgtcattat gcgtggagaa     1620
tatgatgctc tgttgccatg gccgttcaag cagaaagtga cacttatgct gatggatcag     1680
gggtcctctc gccgtcatct gggagatgcg ttcaagcctg accccaacag cagcagcttc     1740
aagaaaccca ccggagagat gaatatcgcc tctggctgcc cagtctttgt cgcccaaact     1800
gttctagaga acgggacgta tattaaagat gatacaatct ttattaaggt catagtggat     1860
acctcggatc tgcctgaccc ctgacaagaa agcagggcgg tggattcagc agaaggtaac     1920
tcctctgggg gggtgagcta gtgtcttcac ggaggtcctc gccctcagaa aggaccttgt     1980
ggcgcagagg aagcagccgg aggaggagaa ggaggtcgag tggctggcag agagccaca     2040 tgtgaaaaca gaccccaacg gatttcctaa taaactagcc acaccactc tgaaggatta     2100 tttatccatc aacaagataa atactgctgt cagagaaggt tttcattttc attttaaaag     2160
atctagtatt aaggtgggaa catatatgct aaaaagaaac atgattttc ttccttaact     2220 taaacaccaa aaagagaaca catgtggggg tagctggagt gtgtacagta cctcgagggc     2280
ttaaaatcat aaacaatcac atactcatcc taaaattcag ggtgcaactc cgtttcaaat     2340
attgtatatt gtctattta                                                  2359
```

<210> SEQ ID NO 4
<211> LENGTH: 2455
<212> TYPE: DNA
<213> ORGANISM: Homo Sapiens

<400> SEQUENCE: 4

```
cgggggagcg cggcgcggcc gccgcgtgcg cgagccgggg ttgcagccca gccgggactt       60
tccagccggc ggcagccgcg gcggtcgtcg gctcttcccc gccccccgtc atggggcagc     120
ccggggagca gaacgctgcg gaccgcggcg gaggacgcgc ccggcgcccc tgagccggcc     180
gagcggcgac ggaccgcgag aactcctctt tcctaaaatg gagtcgagta aaaagatgga     240
ctctcctggc gcgctgcaga ctaacccgcc gctaaagctg cacactgacc gtagtgctgg     300
```

-continued

```
gacgccagtt tttgtccctg aacaaggagg ttacaaggaa aagtttgtga agaccgtgga      360
ggacaagtac aagtgtgaga agtgccacct ggtgctgtgc agcccgaagc agaccgagtg      420
tgggcaccgc ttctgcgaga gctgcatggc ggccctgctg agctcttcaa gtccaaaatg      480
tacagcgtgt caagagagca tcgttaaaga taaggtgttt aaggataatt gctgcaagag      540
agaaattctg gctcttcaga tctattgtcg aatgaaagc agaggttgtg cagagcagtt       600
aacgctggga catctgctgg tgcatttaaa aaatgattgc cattttgaag aacttccatg      660
tgtgcgtcct gactgcaaag aaaaggtctt gaggaaagac ctgcgagacc acgtggagaa      720
ggcgtgtaaa taccgggaag ccacatgcag ccactgcaag agtcaggttc cgatgatcgc      780
gctgcagaaa cacgaagaca ccgactgtcc ctgcgtggtg gtgtcctgcc ctcacaagtg      840
cagcgtccag actctcctga ggagcgagtt gagtgcacac ttgtcagagt gtgtcaatgc      900
ccccagcacc tgtagtttta gcgctatggc ctgcgttttt caggggacaa accagcagat      960
caaggcccac gaggccagct ccgccgtgca gcacgtcaac ctgctgaagg agtggagcaa     1020
ctcgctcgaa aagaaggttt ccttgttgca gaatgaaagt gtagaaaaaa acaagagcat     1080
acaaagtttg cacaatcaga tatgtagctt tgaaattgaa attgagagac aaaaggaaat     1140
gcttcgaaat aatgaatcca aaatccttca tttacagcga gtgatcgaca gccaagcaga     1200
gaaactgaag gagcttgaca aggagatccg gcccttccgg cagaactggg aggaagcaga     1260
cagcatgaag agcagcgtgg agtccctcca gaaccgcgtg accgagctgg agagcgtgga     1320
caagagtgcg gggcaagtgg ctcggaacac aggcctgctg gagtcccagc tgagccggca     1380
tgaccagatg ctgagtgtgc acgacatccg cctagccgac atggacctgc gcttccaggt     1440
cctggagacc gccagctaca atggagtgct catctgaag attcgcgact acaagcggcg       1500
gaagcaggag ccgtcatgg ggaagaccct gtccctttac agccagcctt tctacactgg      1560
ttactttggt tataagatgt gtgccagggt ctacctgaac ggggacggga tggggaaggg      1620
gacgcacttg tcgctgtttt ttgtcatcat gcgtggagaa tatgatgccc tgcttccttg     1680
gccgtttaag cagaaagtga cactcatgct gatggatcag gggtcctctc gacgtcattt     1740
gggagatgca ttcaagcccg accccaacag cagcagcttc aagaagccca ctggagagat     1800
gaatatcgcc tctggctgcc cagtctttgt ggcccaaact gttctagaaa atgggacata     1860
tattaaagat gatacaattt ttattaaagt catagtggat acttcggatc tgcccgatcc     1920
ctgataagta gctggggagg tggatttagc agaaggcaac tcctctgggg gatttgaacc     1980
ggtctgtctt cactgaggtc ctcgcgctca gaaaaggacc ttgtgagacg gaggaagcgg     2040
cagaaggcgg acgcgtgccg gcgggaggag ccacgcgtga gcacacctga cacgttttat     2100
aatagactag ccacacttca ctctgaagaa ttatttatcc ttcaacaaga taaatattgc     2160
tgtcagagaa ggttttcatt ttcatttta aagatctagt taattaaggt ggaaaacata     2220
tatgctaaac aaaagaaaca tgattttct tccttaaact tgaacaccaa aaaaacacac      2280
acacacacac acgtggggat agctggacat gtcagcatgt taagtaaaag gagaatttat     2340
gaaatagtaa tgcaattctg atatcttctt tctaaaattc aagagtgcaa ttttgtttca     2400
aatacagtat attgtctatt tttaaggcct ccaaaaaaaa aaaaaattcc ggccg          2455
```

<210> SEQ ID NO 5
<211> LENGTH: 6
<212> TYPE: PRT
<213> ORGANISM: Homo Sapiens

<400> SEQUENCE: 5

Lys Ala Cys Lys Tyr Arg
1               5

<210> SEQ ID NO 6
<211> LENGTH: 207
<212> TYPE: PRT
<213> ORGANISM: MOUSE SP.

<400> SEQUENCE: 6

Leu Gln Asn Arg Val Thr Glu Leu Glu Ser Val Asp Lys Ser Ala Gly
1               5                   10                  15

Gln Ala Ala Arg Asn Thr Gly Leu Leu Glu Ser Gln Leu Ser Arg His
            20                  25                  30

Asp Gln Thr Leu Ser Val His Asp Ile Arg Leu Ala Asp Met Asp Leu
        35                  40                  45

Arg Phe Gln Val Leu Glu Thr Ala Ser Tyr Asn Gly Val Leu Ile Trp
    50                  55                  60

Lys Ile Arg Asp Tyr Lys Arg Lys Gln Glu Ala Val Met Gly Lys
65                  70                  75                  80

Thr Leu Ser Leu Tyr Ser Gln Pro Phe Tyr Thr Gly Tyr Phe Gly Tyr
                85                  90                  95

Lys Met Cys Ala Arg Val Tyr Leu Asn Gly Asp Gly Met Gly Lys Gly
            100                 105                 110

Thr His Leu Ser Leu Phe Phe Val Ile Met Arg Gly Glu Tyr Asp Ala
        115                 120                 125

Leu Leu Pro Trp Pro Phe Lys Gln Lys Val Thr Leu Met Leu Met Asp
    130                 135                 140

Gln Gly Ser Ser Arg Arg His Leu Gly Asp Ala Phe Lys Pro Asp Pro
145                 150                 155                 160

Asn Ser Ser Ser Phe Lys Lys Pro Thr Gly Glu Met Asn Ile Ala Ser
                165                 170                 175

Gly Cys Pro Val Phe Val Ala Gln Thr Val Leu Glu Asn Gly Thr Tyr
            180                 185                 190

Ile Lys Asp Asp Thr Ile Phe Ile Lys Val Ile Val Asp Thr Ser
        195                 200                 205

<210> SEQ ID NO 7
<211> LENGTH: 56
<212> TYPE: PRT
<213> ORGANISM: MOUSE SP.

<400> SEQUENCE: 7

Ile Gln Ser Leu His Asn Gln Ile Cys Ser Phe Glu Ile Glu Ile Glu
1               5                   10                  15

Arg Gln Lys Glu Met Leu Arg Asn Asn Glu Ser Lys Ile Leu His Leu
            20                  25                  30

Gln Arg Val Ile Asp Ser Gln Ala Glu Lys Leu Lys Glu Leu Asp Lys
        35                  40                  45

Glu Ile Arg Pro Phe Arg Gln Asn
    50                  55

<210> SEQ ID NO 8
<211> LENGTH: 155
<212> TYPE: PRT
<213> ORGANISM: MOUSE SP.

<400> SEQUENCE: 8

```
Leu Ala Leu Gln Val Tyr Cys Arg Asn Glu Gly Arg Gly Cys Ala Glu
 1               5                  10                  15

Gln Leu Thr Leu Gly His Leu Val His Leu Lys Asn Glu Cys Gln
                20                  25                  30

Phe Glu Glu Leu Pro Cys Leu Arg Ala Asp Cys Lys Glu Lys Val Leu
                35                  40                  45

Arg Lys Asp Leu Arg Asp His Val Glu Lys Ala Cys Lys Tyr Arg Glu
 50                  55                  60

Ala Thr Cys Ser His Cys Lys Ser Gln Val Pro Met Ile Lys Leu Gln
 65                  70                  75                  80

Lys His Glu Asp Thr Asp Cys Pro Cys Val Val Ser Cys Pro His
                85                  90                  95

Lys Cys Ser Val Gln Thr Leu Leu Arg Ser Glu Leu Ser Ala His Leu
                100                 105                 110

Ser Glu Cys Val Asn Ala Pro Ser Thr Cys Ser Phe Lys Arg Tyr Gly
                115                 120                 125

Cys Val Phe Gln Gly Thr Asn Gln Gln Ile Lys Ala His Glu Ala Ser
                130                 135                 140

Ser Ala Val Gln His Val Asn Leu Leu Lys Glu
145                 150                 155

<210> SEQ ID NO 9
<211> LENGTH: 62
<212> TYPE: PRT
<213> ORGANISM: MOUSE SP.

<400> SEQUENCE: 9

Thr Val Glu Asp Lys Tyr Lys Cys Glu Lys Cys Arg Leu Val Leu Cys
 1               5                  10                  15

Asn Pro Lys Gln Thr Glu Cys Gly His Arg Phe Cys Glu Ser Cys Met
                20                  25                  30

Ala Ala Leu Leu Ser Ser Ser Pro Lys Cys Thr Ala Cys Gln Glu
                35                  40                  45

Ser Ile Ile Lys Asp Lys Val Phe Lys Asp Asn Cys Cys Lys
 50                  55                  60

<210> SEQ ID NO 10
<211> LENGTH: 244
<212> TYPE: PRT
<213> ORGANISM: MOUSE SP.

<400> SEQUENCE: 10

Ser Gln Ala Glu Lys Leu Lys Glu Leu Asp Lys Glu Ile Arg Pro Phe
 1               5                  10                  15

Arg Gln Asn Trp Glu Glu Ala Asp Ser Met Lys Ser Ser Val Glu Ser
                20                  25                  30

Leu Gln Asn Arg Val Thr Glu Leu Glu Ser Val Asp Lys Ser Ala Gly
                35                  40                  45

Gln Ala Ala Arg Asn Thr Gly Leu Leu Glu Ser Gln Leu Ser Arg His
 50                  55                  60

Asp Gln Thr Leu Ser Val His Asp Ile Arg Leu Ala Asp Met Asp Leu
 65                  70                  75                  80

Arg Phe Gln Val Leu Glu Thr Ala Ser Tyr Asn Gly Val Leu Ile Trp
                85                  90                  95

Lys Ile Arg Asp Tyr Lys Arg Arg Lys Gln Glu Ala Val Met Gly Lys
                100                 105                 110
```

```
Thr Leu Ser Leu Tyr Ser Gln Pro Phe Tyr Thr Gly Tyr Phe Gly Tyr
        115                 120                 125

Lys Met Cys Ala Arg Val Tyr Leu Asn Gly Asp Gly Met Gly Lys Gly
    130                 135                 140

Thr His Leu Ser Leu Phe Phe Val Ile Met Arg Gly Glu Tyr Asp Ala
145                 150                 155                 160

Leu Leu Pro Trp Pro Phe Lys Gln Lys Val Thr Leu Met Leu Met Asp
                165                 170                 175

Gln Gly Ser Ser Arg Arg His Leu Gly Asp Ala Phe Lys Pro Asp Pro
            180                 185                 190

Asn Ser Ser Ser Phe Lys Lys Pro Thr Gly Glu Met Asn Ile Ala Ser
            195                 200                 205

Gly Cys Pro Val Phe Val Ala Gln Thr Val Leu Glu Asn Gly Thr Tyr
        210                 215                 220

Ile Lys Asp Asp Thr Ile Phe Ile Lys Val Ile Val Asp Thr Ser Asp
225                 230                 235                 240

Leu Pro Asp Pro
```

<210> SEQ ID NO 11
<211> LENGTH: 153
<212> TYPE: PRT
<213> ORGANISM: MOUSE SP.

<400> SEQUENCE: 11

```
Gly Val Leu Ile Trp Lys Ile Arg Asp Tyr Lys Arg Arg Lys Gln Glu
1               5                   10                  15

Ala Val Met Gly Lys Thr Leu Ser Leu Tyr Ser Gln Pro Phe Tyr Thr
            20                  25                  30

Gly Tyr Phe Gly Tyr Lys Met Cys Ala Arg Val Tyr Leu Asn Gly Asp
        35                  40                  45

Gly Met Gly Lys Gly Thr His Leu Ser Leu Phe Phe Val Ile Met Arg
    50                  55                  60

Gly Glu Tyr Asp Ala Leu Leu Pro Trp Pro Phe Lys Gln Lys Val Thr
65                  70                  75                  80

Leu Met Leu Met Asp Gln Gly Ser Ser Arg Arg His Leu Gly Asp Ala
                85                  90                  95

Phe Lys Pro Asp Pro Asn Ser Ser Ser Phe Lys Lys Pro Thr Gly Glu
            100                 105                 110

Met Asn Ile Ala Ser Gly Cys Pro Val Phe Val Ala Gln Thr Val Leu
        115                 120                 125

Glu Asn Gly Thr Tyr Ile Lys Asp Asp Thr Ile Phe Ile Lys Val Ile
    130                 135                 140

Val Asp Thr Ser Asp Leu Pro Asp Pro
145                 150
```